United States Patent [19]
Dirbas

[11] Patent Number: 6,125,350
[45] Date of Patent: *Sep. 26, 2000

[54] MEDICAL INFORMATION LOG SYSTEM

[75] Inventor: Frederick Mark Dirbas, Menlo Park, Calif.

[73] Assignee: Software for Surgeons, Menlo Park, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/531,256

[22] Filed: Sep. 20, 1995

Related U.S. Application Data

[63] Continuation-in-part of application No. 08/458,905, Jun. 2, 1995.

[51] Int. Cl.[7] .................................................. G06F 159/00
[52] U.S. Cl. ...................................... 705/2; 705/3
[58] Field of Search ............................. 705/1–4; 707/10, 707/104

[56] References Cited

U.S. PATENT DOCUMENTS

| | | | |
|---|---|---|---|
| 4,878,175 | 10/1989 | Norden-Paul et al. | 364/401 M |
| 5,077,666 | 12/1991 | Brimm et al. | 364/408 |
| 5,262,943 | 11/1993 | Thibado et al. | 364/401 M |
| 5,327,341 | 7/1994 | Whalen et al. | 364/401 M |

FOREIGN PATENT DOCUMENTS

0457000A2  11/1991  European Pat. Off. .

OTHER PUBLICATIONS

Wyatt, "Clinical Data Systems, Part 3: Development and Evaluation", Lancet, V344, N8938, P1682(7), Dec. 17, 1994, Dialog File 148, Accession No. 07620766.

Ornstein et al. "The Computer–Based Medical Record: Current Status", Journal of Family Practice, v35, N5, 556(10), Nov. 1992, Dialog File 149, Accession No. 01374326.

*Primary Examiner*—Frantzy Poinvil
*Attorney, Agent, or Firm*—Townsend & Townsend & Crew LLP

[57] ABSTRACT

A computer system (100) to provide a medical information log system (202). A mouse (107) and/or a keyboard (106) is used to input data (400) for various medical log entries. These log entries are associated with a medical visit, and they contain information related to the doctor (1020) and the type of said medical visit (1040). Each medical visit has only one log entry associated with it. The inputted data are stored within an organized database located in the computer's memory (103). The computer's controller (101) is used to track the inputted data for various desired information. This information can be used for record keeping, outcome analysis, research, teaching, quality assurance, and/or billing. The inputted data are displayed on display (105) when desired.

17 Claims, 49 Drawing Sheets

Click on a Procedure to Select It

| | | |
|---|---|---|
| Search | Find All | Page Up |
| Clear | Cancel | Page Down |

| Section | Procedure |
|---|---|
| | SKIN |
| Skin and Soft Tissues | Major lymphadenectomy |
| Skin and Soft Tissues | Major excision for skin neoplasm |
| Skin and Soft Tissues | Radical excision of soft tissue tumor |
| Skin and Soft Tissues | Other major skin procedure |
| | HEAD AND NECK |
| Head and Neck | Lip resection |
| Head and Neck | Tongue resection |
| Head and Neck | Floor of mouth/buccal mucosa resect |
| Head and Neck | Parotidctomy |
| Head and Neck | Resect of other salivary glands |
| Head and Neck | Radical neck dissection |
| Head and Neck | Resection of mandible or maxilla |
| Head and Neck | Tracheostomy |
| Head and Neck | Other major head and neck |
| | BREAST |
| Breast | Breast biopsy |
| Breast | Simple mastectomy |
| Breast | Modified radical mastectomy |
| Breast | Radical mastectomy |
| Breast | Excis bx/quadrantect with ax dissect |
| Breast | Breast reconstruction |
| Breast | Other major breast surgury |
| | ALIMENTARY TRACT |
| Alimentary Tract | Esophagectomy |
| Alimentary Tract | Esophago-gastrectomy |
| Alimentary Tract | Antireflux procedure (open) |
| Alimentary Tract | Antireflux procedure (laparoscopic) |
| Alimentary Tract | Esophageal bypass procedure |
| Alimentary Tract | Repair of esophageal perforation |
| Alimentary Tract | Operations for esophageal stenosis |
| Alimentary Tract | Esophageal diverticulectomy |
| Alimentary Tract | Other major esophageal operations |
| Alimentary Tract | Gastrostomy (open) |
| Alimentary Tract | Gastrostomy (laparoscopic) |
| Alimentary Tract | Gastric resection; partial (open) |
| Alimentary Tract | Gastric resection; partial (lap) |
| Alimentary Tract | Gastric resection; total |
| Alimentary Tract | Vagot; trunc/select with drain (open) |
| Alimentary Tract | Vagot; trunc/select with drain (lap) |
| Alimentary Tract | Repair of gastric peforation |
| Alimentary Tract | Prox gastric vagot; high select (op) |
| Alimentary Tract | Prox gastric vagot; high select (lap) |
| Alimentary Tract | Gastroc reduct for morbid obesity |
| Alimentary Tract | Other major gastric cases |
| Alimentary Tract | Enterolysis |
| Alimentary Tract | Enterectomy (open) |
| Alimentary Tract | Enterectomy (laparoscopic) |
| Alimentary Tract | Repair of duodenal perforation |
| Alimentary Tract | Repair of jej/ileal perforation |
| Alimentary Tract | Ileostomy (not with colectomy) |
| Alimentary Tract | Jej/ileal diverticulectomy |
| Alimentary Tract | Other major small bowel operation |
| Alimentary Tract | Appendectomy (open) |
| Alimentary Tract | Appendectomy (laparoscopic) |
| Alimentary Tract | Colostomy (all types) |
| Alimentary Tract | Colostomy closure |
| Alimentary Tract | Colostomy; partial (open) |
| Alimentary Tract | Cloostomy; partial (laparoscopic) |
| Alimentary Tract | Colect; tot or subtot w/ileost (open) |
| Alimentary Tract | Colect; tot or subtot w/ileost (lap) |

FIG. 5

Click on a numeric value to select a CPT code.
Click on a text field to see more text.

620

| System | Region | Category | Procedure | | Search | Find All | Code |
|---|---|---|---|---|---|---|---|
| Integumentary System | SKIN | EXCISION-DEBRIDE | Debridement; skin, subcutaneous tissue, and muscle | | | | 11043 |

Clear current CPT code    Cancel

FIG. 6B

Click on a numeric value to select a CPT code.
Click on a text field to see more text.

[ Search ]  [ Find All ]

← 630

| System | Region | Category | Procedure | Code |
|---|---|---|---|---|
| Integumentary System | SKIN | INCISION AND | INCISION AND DRAINAGE | |
| Integumentary System | SKIN | INCISION AND | *Acne surgery (eg, marsupialization, opening or removal of | 10040 |
| Integumentary System | SKIN | INCISION AND | *Incision and drainage of absces (eg, carbuncle, | 10060 |
| Integumentary System | SKIN | INCISION AND | Incision and drainage of abscess (eg, carbuncle, suppurative | 10061 |
| Integumentary System | SKIN | INCISION AND | *Incision and drainage of pilonidal cyst; simple | 10080 |
| Integumentary System | SKIN | INCISION AND | Incision and drainage of pilonidal cyst; complicated | 10081 |
| Integumentary System | SKIN | INCISION AND | *Incision and removal of foreign body, subcutaneous | 10120 |
| Integumentary System | SKIN | INCISION AND | Incision and removal of foreign body, subcutaneous tissues; | 10121 |
| Integumentary System | SKIN | INCISION AND | *Incision and drainage of hematoma, seroma or fluid | 10140 |
| Integumentary System | SKIN | INCISION AND | *Puncture aspiration of abscess, hematoma, bulla, or cyst | 10160 |
| Integumentary System | SKIN | INCISION AND | Incision and drainage, complex, postoperative wound | 10180 |
| Integumentary System | SKIN | EXCISION-DEBRIDE | EXCISION-DEBRIDEMENT | |
| Integumentary System | SKIN | EXCISION-DEBRIDE | *Debridement of extensive eczematous or infected skin; up | 11000 |
| Integumentary System | SKIN | EXCISION-DEBRIDE | Debridement of extensive eczematous or infected skin; each | 11001 |
| Integumentary System | SKIN | EXCISION-DEBRIDE | Debridement; skin, partial thickness | 11040 |
| Integumentary System | SKIN | EXCISION-DEBRIDE | Debridement; skin, full thickness | 11041 |
| Integumentary System | SKIN | EXCISION-DEBRIDE | Debridement; skin, and subcutaneous tissue skin | 11042 |
| Integumentary System | SKIN | EXCISION-DEBRIDE | Debridement; skin, subcutaneous tissue, and muscle | 11043 |
| Integumentary System | SKIN | EXCISION-DEBRIDE | Debridement; subcutaneous tissue, muscle, and bone | 11044 |
| Integumentary System | SKIN | PARING OR | PARING OR CURETTEMENT | |
| Integumentary System | SKIN | PARING OR | *Paring or curettement of benign hyperkeratotic skin lesion | 11050 |
| Integumentary System | SKIN | PARING OR | Paring or curettement of benign hyperkeratotic skin lesion | 11051 |
| Integumentary System | SKIN | PARING OR | Paring or curettement of benign hyperkeratotic skin lesion | 11052 |
| Integumentary System | SKIN | BIOPSY | BIOPSY | |
| Integumentary System | SKIN | BIOPSY | Biopsy of skin, subcutaneous tissue and/or mucous | 11100 |
| Integumentary System | SKIN | BIOPSY | Biopsy of skin, subcutaneous tissue and/or mucous | 11101 |
| Integumentary System | SKIN | REMOVAL OF SKIN | REMOVAL OF SKIN TAGS | |

[ Clear current CPT code ]   [ Cancel ]

FIG. 6C

Click on a numeric value to select a CPT code.
Click on a text field to see more text.

[ Search ]  [ Find All ]  [ Find Preferred ]

| System | Region | Category | Procedure | Preferred | Code |
|---|---|---|---|---|---|
| Anesthesia | Head | | Anesthesia for procedures on integumentary | ☐ | 00100 |
| Anesthesia | Head | | Anesthesia for procedures on integumentary | ☐ | 00102 |
| Anesthesia | Head | | Anesthesia for procedures on integumentary | ☒ | 00103 |
| Anesthesia | Head | | Anesthesia for electroconvulsive therapy | ☐ | 00104 |
| Anesthesia | Head | | Anesthesia for procedures on external, middle, and | ☐ | 00120 |
| Anesthesia | Head | | Anesthesia for procedures on external, middle, and | ☒ | 00124 |
| Anesthesia | Head | | Anesthesia for procedures on external, middle, and | ☐ | 00126 |
| Anesthesia | Head | | Anesthesia for procedures on eye; not otherwise | ☐ | 00140 |
| Anesthesia | Head | | Anesthesia for procedures on eye; lens surgery | ☐ | 00142 |
| Anesthesia | Head | | Anesthesia for procedures on eye; corneal | ☐ | 00144 |
| Anesthesia | Head | | Anesthesia for procedures on eye; vitrectomy | ☒ | 00145 |
| Anesthesia | Head | | Anesthesia for procedures on eye; iridectomy | ☐ | 00147 |
| Anesthesia | Head | | Anesthesia for procedures on eye; | ☐ | 00148 |
| Anesthesia | Head | | Anesthesia for procedures on nose accessory | ☐ | 00160 |
| Anesthesia | Head | | Anesthesia for procedures on nose and accessory | ☐ | 00162 |
| Anesthesia | Head | | Anesthesia for procedures on nose and accessory | ☒ | 00164 |
| Anesthesia | Head | | Anesthesia for intraoral procedures, including | ☐ | 00170 |
| Anesthesia | Head | | Anesthesia for intraoral procedures, including | ☐ | 00172 |
| Anesthesia | Head | | Anesthesia for intraoral procedures, including | ☐ | 00174 |
| Anesthesia | Head | | Anesthesia for intraoral procedures, including | ☐ | 00176 |
| Anesthesia | Head | | Anesthesia for procedures on facial bones; not | ☐ | 00190 |
| Anesthesia | Head | | Anesthesia for procedures on facial bones; radical | ☐ | 00192 |
| Anesthesia | Head | | Anesthesia for intracranial procedures; not | ☐ | 00210 |
| Anesthesia | Head | | Anesthesia for intracranial procedures; subdural | ☐ | 00212 |
| Anesthesia | Head | | Anesthesia for intracranial procedures; burr holes | ☐ | 00214 |
| Anesthesia | Head | | Anesthesia for intracranial procedures; elevation of | ☐ | 00215 |
| Anesthesia | Head | | Anesthesia for intracranial procedures; vascular | ☐ | 00216 |
| Anesthesia | Head | | Anesthesia for intracranial procedures; procedures | ☐ | 00218 |
| Anesthesia | Head | | Anesthesia for intracranial procedures; spinal fluid | ☐ | 00220 |
| Anesthesia | Head | | Anesthesia for intracranial procedures; | ☐ | 00222 |

[ Clear current CPT code ]  [ Cancel ]

General Surgery Case Counter

File  Edit  Database  Options  Reports  Window  System  Administrator

Report Dialog

RESIDENT RECORD
SURGICAL OPERATIVE LOG SYSTEM
Residency Review Committee for General Surgery Case Summary [by Date]

| # | Date | Name | MR# | Operation | Sect | CPT | St | Hospital | Staff |
|---|------|------|-----|-----------|------|-----|-----|----------|-------|
| 1 | / / | Smith | | | | | TA | Palo Alto | Dirbas |
| 2 | / / | Lucero | | | | | TA | Palo Alto | Dirbas |
| 3 | / / | Teixeira | | | | | TA | Palo Alto | Dirbas |
| 4 | / / | White | | | | | TA | Palo Alto | Johnson |
| 5 | 06/01/95 | Galloway | | | | | TA | Palo Alto | Dirbas |
| 6 | 06/01/95 | George | | | | | | Stanford | Dirbas |
| 7 | 06/01/95 | Harrison | | | | | | | |

[Print Setup]  [Print Preview]  [Print]  [Close]

Outcomes

Followup Required? ▷

Followup Phone Call Required? ▷

Followup Items

Patient
Followup

Outcome

Cancer Diagnosis? ▷

Date of Last Contact / /

Date of Birth / /

Date of Next Appointment / /

Death? ▷

[ Main Data Entry (p. 1) ]  [ Quality Assurance (p. 2) ]

FIG. 21

Table 1

Structure for table: c:\casecntr\dbf\gsaccsbk.dbf
Number of data records: 8
Date of last update: 09/04/95
Memo file block size: 64
Code Page: 0

| Field | Field Name | Type | Width | Dec | Index | Collate |
|---|---|---|---|---|---|---|
| 1 | CASEID | Numeric | 6 | | Asc | Machine |
| 2 | CASEDATE | Date | 8 | | Asc | Machine |
| 3 | PATFNAME | Character | 30 | | Asc | Machine |
| 4 | PATMNAME | Character | 2 | | Asc | Machine |
| 5 | PATLNAME | Character | 30 | | Asc | Machine |
| 6 | PATINITIAL | Character | 3 | | Asc | Machine |
| 7 | PATDOB | Date | 8 | | Asc | Machine |
| 8 | PATAGE | Character | 6 | | Asc | Machine |
| 9 | PATMRN | Character | 15 | | Asc | Machine |
| 10 | PATSEX | Character | 1 | | Asc | Machine |
| 11 | OUTPTARRIV | Character | 3 | | | |
| 12 | INPATIENT | Character | 3 | | | |
| 13 | LOCATION | Character | 30 | | | |
| 14 | BRFOPDESC | Character | 100 | | | |
| 15 | OPNOTEDICT | Character | 3 | | | |
| 16 | CPTCODE | Character | 10 | | | |
| 17 | SURFULNAME | Character | 80 | | Asc | Machine |
| 18 | SURPGYYR | Character | 10 | | Asc | Machine |
| 19 | HOSPITAL | Character | 30 | | Asc | Machine |
| 20 | SURGSERV | Character | 30 | | Asc | Machine |
| 21 | ATTNDFNAME | Character | 20 | | Asc | Machine |
| 22 | ATTNDLNAME | Character | 20 | | Asc | Machine |
| 23 | SURPROGRAM | Character | 25 | | Asc | Machine |
| 24 | PATHHISTORY | Memo | 10 | | | |
| 25 | OPFINDINGS | Character | 100 | | | |
| 26 | PATHOLOGY | Character | 100 | | Asc | Machine |
| 27 | COMPYESNO | Character | 3 | | Asc | Machine |
| 28 | PATOUTCOME | Character | 40 | | | |
| 29 | PATFOLLUP | Memo | 10 | | | |
| 30 | COMPCAT1 | Character | 10 | | | |
| 31 | COMPCAT2 | Character | 10 | | | |
| 32 | COMPCAT3 | Character | 10 | | | |
| 33 | COMPCAT4 | Character | 10 | | | |
| 34 | COMPLIC1 | Character | 40 | | | |
| 35 | COMPLIC2 | Character | 40 | | | |
| 36 | COMPLIC3 | Character | 40 | | | |
| 37 | COMPLIC4 | Character | 40 | | | |
| 38 | COMPDESC | Memo | 10 | | | |
| 39 | FUPREQ | Character | 3 | | Asc | Machine |
| 40 | FUPCALLREQ | Character | 3 | | Asc | Machine |
| 41 | FUPITEMS | Character | 100 | | | |
| 42 | CANCERDX | Character | 3 | | Asc | Machine |
| 43 | LSTCONTACT | Date | 8 | | Asc | Machine |
| 44 | NXTAPPT | Date | 8 | | Asc | Machine |
| 45 | DEATH | Character | 3 | | Asc | Machine |
| 46 | DEATHDATE | Date | 8 | | | |
| ** Total ** | | | 1083 | | | |

FIG. 23

Table 2

Structure for table: c:\casecntr\dbf\opdata.dbf
Number of data records: 40
Date of last update: 09/04/95
Code Page: 0

| Field | Field Name | Type | Width | Dec | Index | Collate |
|---|---|---|---|---|---|---|
| 1 | OPDATAID | Numeric | 6 | | Asc | Machine |
| 2 | CASEID | Numeric | 6 | | Asc | Machine |
| 3 | OPERID | Numeric | 4 | | | |
| 4 | CASEOPID | Numeric | 1 | | | |
| 5 | CODING | Character | 3 | | | |
| 6 | CPTCODE | Character | 10 | | | |
| 7 | PROCNOTE | Character | 100 | | | |
| 8 | ICD9CODE | Character | 10 | | | |
| ** Total ** | | | 141 | | | |

FIG. 24

Table 3

Structure for table: c:\casecntr\dbf\opdx.dbf
Number of data records: 43
Date of last update: 09/04/95
Code Page: 0

| Field | Field Name | Type | Width | Dec | Index | Collate |
|---|---|---|---|---|---|---|
| 1 | CASEID | Numeric | 6 | | Asc | Machine |
| 2 | CASEDXID | Numeric | 1 | | Asc | Machine |
| 3 | PREOPDX | Character | 50 | | Asc | Machine |
| 4 | POSTOPDX | Character | 50 | | Asc | Machine |
| 5 | ICD9CODE | Character | 10 | | Asc | Machine |
| 6 | PRIMARY | Logical | 1 | | Asc | Machine |
| ** Total ** | | | 119 | | | |

Additional Surgeons

| | |
|---|---|
| Principal Surgeon | Ken Lewis |
| Additional Surgeon #1 | Frederick Dirbas, M.D. |
| Additional Surgeon #2 | |
| Additional Surgeon #3 | |
| Additional Surgeon #4 | |

Procedures
- Other major head and neck resection
- Parotidectomy

|  | PS | AS1 | AS2 | AS3 | AS4 |
|---|---|---|---|---|---|
|  | TA | SC | ☐ | ☐ | ☐ |
|  | TA | SJ | ☐ | ☐ | ☐ |
|  | ☐ | ☐ | ☐ | ☐ | ☐ |
|  | ☐ | ☐ | ☐ | ☐ | ☐ |
|  | ☐ | ☐ | ☐ | ☐ | ☐ |

Save / Cancel

FIG. 31

Table 4

Structure for table: c:\casecntr\dbf\opstatus.dbf
Number of data records: 48
Date of last update: 09/04/95
Code Page: 0

| Field | Field Name | Type | Width | Dec | Index | Collate |
|---|---|---|---|---|---|---|
| 1 | OPSTATUSID | Numeric | 6 | | Asc | Machine |
| 2 | OPDATAID | Numeric | 6 | | Asc | Machine |
| 3 | SURGID | Numeric | 6 | | Asc | Machine |
| 4 | SURGSTATUS | Character | 2 | | Asc | Machine |
| 5 | SURGPGY | Character | 10 | | Asc | Machine |
| 6 | WHICHSURG | Character | 3 | | Asc | Machine |
| ** Total ** | | | 34 | | | |

| # | Date | Name | MR# | Operation | Sect CPT | St | Hospital | Staff |
|---|------|------|-----|-----------|----------|----|----|-------|
| 1 | / / | Lucero | 541072-8889 | Insert/femoral her | AB6 | TA | Palo Alto | Dirbas |
| 2 | / / | Teixeira | 554-64-6390 | Insert of levine or | VA8 | TA | Palo Alto | Dirbas |
| 3 | / / | White | 432-98-2960 | Removal of subcutane | MIS | | | |
| 4 | 05/05/95 | Maltby | 555-54-0327 | Lip resection | HEA | FA | Palo Alto | Johnson |
| 5 | 06/01/95 | Galloway | 536-20-5152 | Abdomino-perineal re | AL4 | TA | Palo Alto | Dirbas |
| 6 | 06/01/95 | George | 553-18-4630 | Inguinal/femoral her | AB6 | | Stanford | Dirbas |
| 7 | 06/01/95 | Harrison | 574-54-0327 | Antireflux procedure | AL1 | TA | Palo Alto | Dirbas |
| 8 | 06/12/95 | Smith | 489-32-2471 | Other major head and | HEA | SJ | Lebanon V | Dirbas |
| 9 | 06/12/95 | White | 566-77-8923 | Radical excision of | SKI | SJ | | Dirbas |
| 10 | 06/12/95 | Mucho | | Arthroscopy | ORT | | | |
| 11 | 06/12/95 | Maas | | Antireflux procedure | AL1 | | | |
| 12 | 06/12/95 | Blatchley | | Vagot; trunc/select | AL2 | | | |
| 13 | 06/12/95 | False | | Repair of esophageal | AL1 | | | |
| 14 | 09/04/95 | Lewis | 44443333 | Radical excision of | SKI | | | |
| 15 | 09/04/95 | L | | Tracheostomy | HEA | | | |

RESIDENT RECORD
SURGICAL OPERATIVE LOG SYSTEM
Residency Review Committee for General Surgery
Case Summary by Date

FIG. 39

Report Dialog

Define Criteria for QA Document

Patient First Name | Patient Last Name | Patient MR#
--- | --- | ---
 | g |

Leave fields blank to display all records.

Highlight a record then choose Print or Print Preview

| First Name | Last Name | MR # | Date |
|---|---|---|---|
| Duane | Galloway | 536-20-5152 | 06/01/95 |
| Lawrence | George | 553-18-4630 | 06/01/95 |

Show | Clear All

Print Setup | Print Preview | Print | Close

FIG. 45

Structure for table: c:\casecntr\dbf\surgserv.dbf
Number of data records: 19
Date of last update: 10/06/94
Code Page: 0

| Field | Field Name | Type | Width | Dec | Index | Collate |
|---|---|---|---|---|---|---|
| 1 | SURGSERV | Character | 30 | | | |
| ** Total ** | | | 31 | | | |

FIG. 46A

Structure for table: c:\casecntr\dbf\diagnos.dbf
Number of data records: 30
Date of last update: 05/25/95
Code Page: 0

| Field | Field Name | Type | Width | Dec | Index | Collate |
|---|---|---|---|---|---|---|
| 1 | DIAGNOSIS | Character | 50 | | | |
| ** Total ** | | | 51 | | | |

FIG. 46B

Structure for table: c:\casecntr\dbf\reports.dbf
Number of data records: 7
Date of last update: 04/14/95
Code Page: 0

| Field | Field Name | Type | Width | Dec | Index | Collate |
|---|---|---|---|---|---|---|
| 1 | REPORTID | Numeric | 3 | | | |
| 2 | REPORTNAME | Character | 40 | | | |
| 3 | REPORTTYPE | Character | 10 | | | |
| ** Total ** | | | 54 | | | |

FIG. 46C

Structure for table: c:\casecntr\dbf\gscscntr.dbf
Number of data records: 362
Date of last update: 03/15/95
Code Page: 0

| Field | Field Name | Type | Width | Dec | Index | Collate |
|---|---|---|---|---|---|---|
| 1 | OPERID | Numeric | 4 | | Asc | Machine |
| 2 | ENTRYCAT | Character | 9 | | | |
| 3 | SECTION | Character | 3 | | | |
| 4 | OPERATION | Character | 40 | | | |
| 5 | OPTYPE | Character | 15 | | | |
| 6 | CPTCODE | Character | 10 | | | |
| 7 | LAP_THOR | Logical | 1 | | | |
| ** Total ** | | | 83 | | | |

FIG. 46D

MEDICAL INFORMATION LOG SYSTEM

CROSS REFERENCE TO RELATED APPLICATIONS

This application is a continuation-in-part of U.S. patent application Ser. No. 08/458,905, filed Jun. 2, 1995 (pending), which is incorporated herein by reference in its entirety for all purposes.

COPYRIGHT NOTICE

A portion of the disclosure of this patent document contains material which is subject to copyright protection. The copyright owner has no objection to the photographic reproduction by anyone of the patent document or the patent disclosure in exactly the form it appears in the Patent and Trademark Office patent file or records, but otherwise reserves all copyright rights whatsoever.

BACKGROUND OF THE INVENTION

The present invention is directed to a medical information log system, and more particularly to advanced features in a surgical operative log system.

The ReSOLution package from Information Science Associates (ISA) is a DOS based program created specifically for the Accreditation Council for Graduate Medical Education (ACGME) and Residency Review Committee (RRC) for surgery. The program is not network compatible, is not cross-platform capable, and does not incorporate Current Procedural Terminology (CPT) menus or coding for forms for the American College of Surgeons (ACS). CPT is a standard numerical coding scheme. It can download information directly to ACGME/RRC reporting diskettes which are the required method of reporting operative data by surgical residents and surgical training programs to the ACGME and RRC.

Summit from Summit Medical is a specific package for tracking pre, peri, and post operative variables, as well as outcomes for cardiothoracic surgery. While fairly comprehensive, it not cross-platform capable, and does not address all the needs of cardiothoracic residents. Specifically, it does not attempt to assist cardiothoracic surgery residents with completing required forms for the American Board of Thoracic Surgery certification (ABTS—the RCC equivalent for cardiothoracic surgery).

The TRACS package was designed specifically to track trauma and, to a less extent, critical care patients on surgical services. This package does not do coding for the RRC or the ACS, and does not cover any areas of General Surgery other than trauma, let alone other surgical specialties.

Surgical Procedure Log™ (SPL) from Medical Software Solutions, Inc. is a member of the FileMaker Database market. Databases were created in FileMaker Pro, and these databases were applied to multiple specialties. FileMaker often has problems when dealing with large databases. For example, the current FileMaker version does not support files larger than 32 MByte (about 32K operations). In addition, SPL does not incorporate ACS coding forms.

The package from the American College of Surgeons (ACS) includes a program written in FoxPro (Windows version only) limited to general cancer database (outcomes package). This is not an operative log, and it does not generate RRC, ACS, or similar reports.

VascuBase for Vascular Surgeons from Consensus Medical Systems, Inc. is a surgical log and outcomes package for vascular surgeons only. This package includes statistics and some graphics, but it does not generate report forms for residents for the RRC. Thus, this package is limited by specialty and directed at practicing surgeons, but not surgeons in training (residents).

Most surgical log systems are for full departments only. Thus, a system for either a full department or individual use is needed. Additionally, a system which functions across multiple specialties is desirable, and enhanced system functionality is desirable.

SUMMARY OF THE INVENTION

In the preferred embodiment, the present invention utilizes a computer system to provide a medical information log system. A mouse and/or a keyboard is used to input data for various medical log entries. These log entries are associated with a medical visit, and they contain information related to the doctor and the type of said medical visit. Each medical visit has only one log entry associated with it. The inputted data are stored within an organized database located in the computer's memory. The computer's controller is used to track the inputted data for various information. This information includes record keeping, outcome analysis, research, teaching, quality assurance, and/or billing. The inputted data are displayed when desired.

These and other advantages will become apparent to those skilled in this art upon a reading of the following detailed description of the invention, which should be taken in conjunction with the accompanying drawings.

BRIEF DESCRIPTION OF THE DRAWINGS

FIG. 5 is an example of a screen display for finding an RRC code from a list during data entry;

FIGS. 6A–D are examples of screen displays for finding a CPT code from a list during data entry;

FIG. 8 is an example of the main data entry screen display;

FIG. 14 is an example of a screen display of a case summary report by date;

FIG. 15 is an example of a screen display for entering and retrieving image data;

FIG. 19 is another example of a screen display for entering main data;

FIG. 21 is an example of a screen display for entering outcomes data;

FIG. 23 is an example of Table 1 which includes the information associated with the fields listed under the Field Name column (e.g., CASEID, CASEDATE, PATFNAME, PATMNAME, PATLNAME, etc.);

FIG. 24 an example of Table 2 which includes information related to the fields included under the Field Name column (e.g., OPDATAID, CASEID, OPERID, CASEOPID, etc.);

FIG. 31 is an example of a screen display for entering additional surgeons;

FIG. 35 is an example of a screen display for viewing outcomes information;

FIG. 37 is an example of a screen display for the find case records feature;

FIG. 45 is an example of a screen display for the QA document; and

FIGS. 46A–D provide additional tables which can be used to assist in the generation of the above-described screens.

DESCRIPTION OF PREFERRED EMBODIMENTS

The present invention is a medical information log system which can be used for either a full department or individual use. In addition, the present invention provides a single package which (1) functions across multiple specialties and (2) can be modified to accommodate an additional specialty. The present computer application system can hold an extremely large number of operation records. Additionally, reports related to these operation records can be quickly generated.

Figure 1:
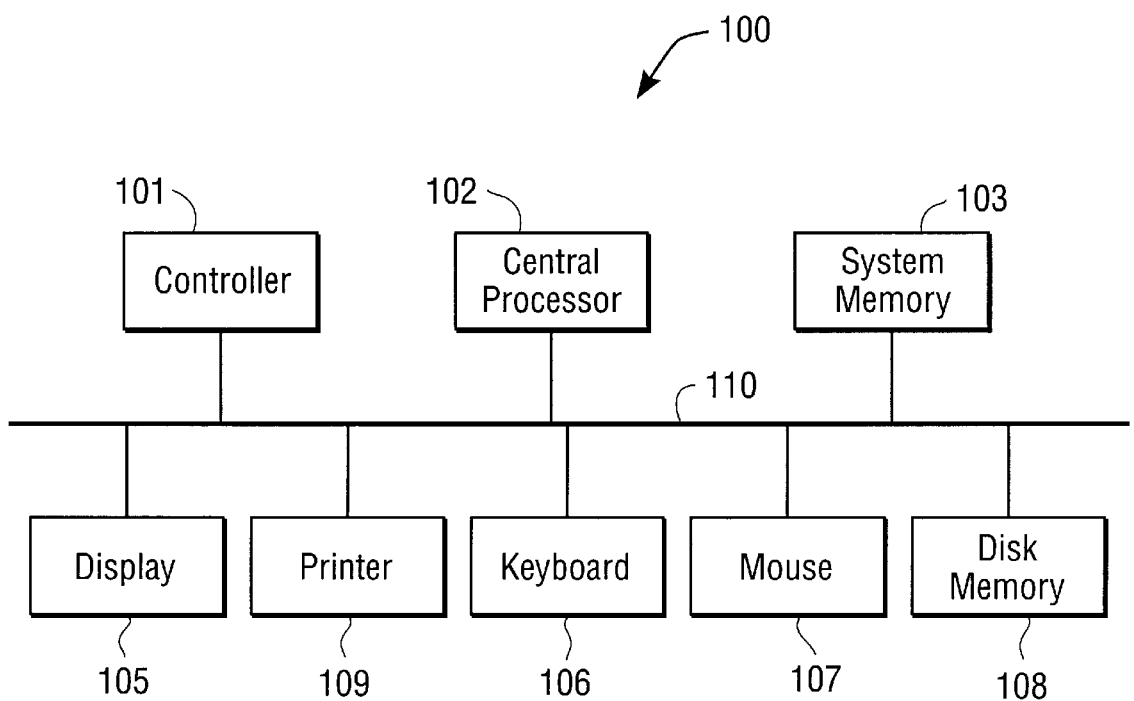
FIG. 1 is a block diagram of a computer system in which the invention may be embodied.

FIG. 1 is a block diagram of a computer system in which the invention may be embodied. In the preferred embodiment, the invention is implemented on a computer system 100 having a processor 102, a system memory 103, a display device 105, a keyboard 106, a mouse 107, a disk memory 108, an I/O controller 101, a printer 109, and an interconnecting device 110, such as a system bus. Disk memory 108 may consist of hard disk(s), floppy disk(s), CD-ROM(s), PIMIA or other plug-in memory device(s), and the like.

Figure 2:
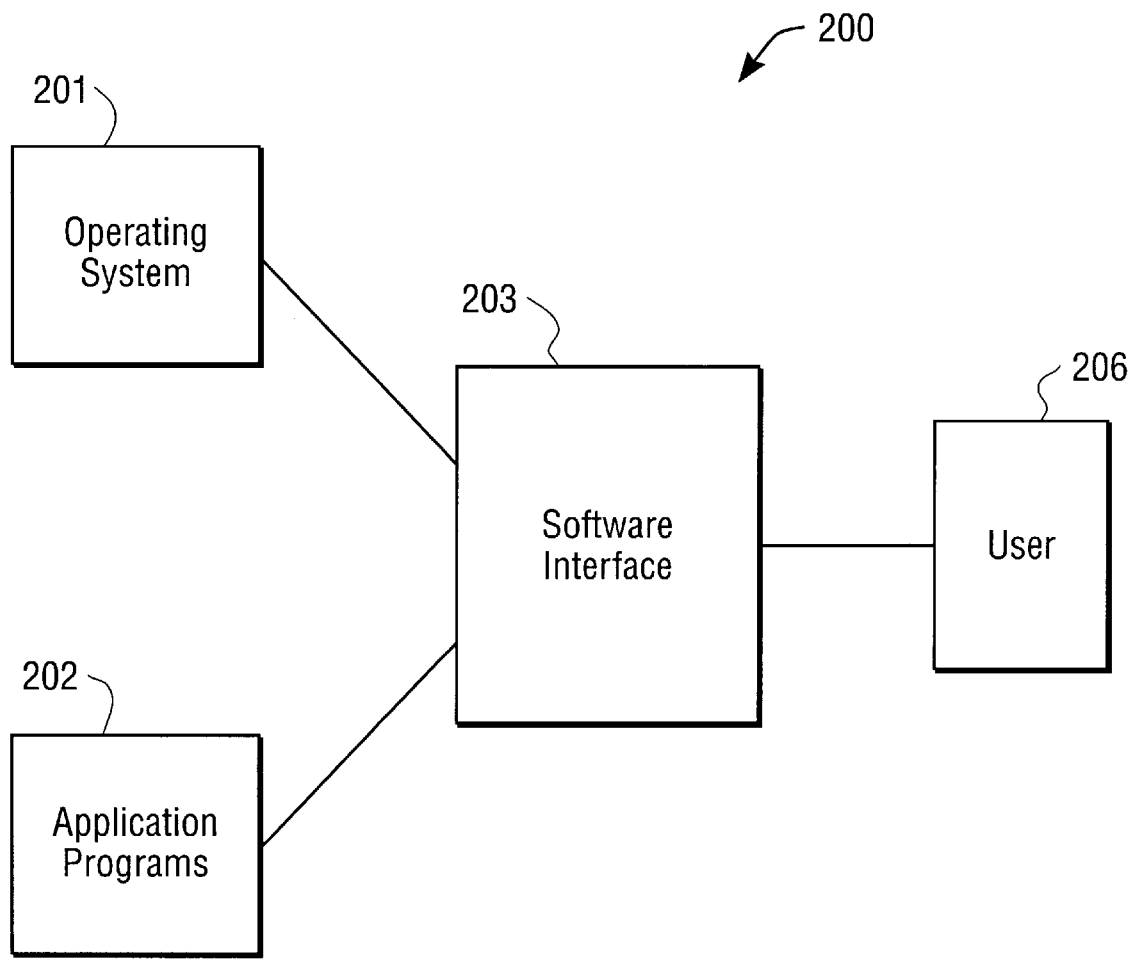
FIG. 2 is a block diagram of a computer software system used in the preferred embodiment.

FIG. 2 is a block diagram of a computer software system used in the preferred embodiment. A computer software system 200 is used to program the computer system of FIG. 1. Software system 200 is stored in system memory 103 and/or on disk memory 108. Thus, the software for the present invention can be provided on a floppy disk(s). Software system 200 programs the central processor 102 to display a graphic user interface (GUI) on display monitor 105. In the preferred embodiment, software interface 203 provides an interface between a user 206, an operating system 201, and a computer application 202. It will be apparent that one of ordinary skill in the art, informed by this application, could implement the invention in other operating environments.

In the preferred embodiment, computer application 202 is a surgical operative log system written in FoxPro. This operative log system can also be written in FileMaker, and the like. Computer application 202 is compatible with DOS, UNIX, Mac and Windows systems. While a surgical operative log system is provided in the preferred embodiment, the present invention also provides a log system for any type of medical information including medical visits, minor medical procedures, and medical operations.

Figure 3:
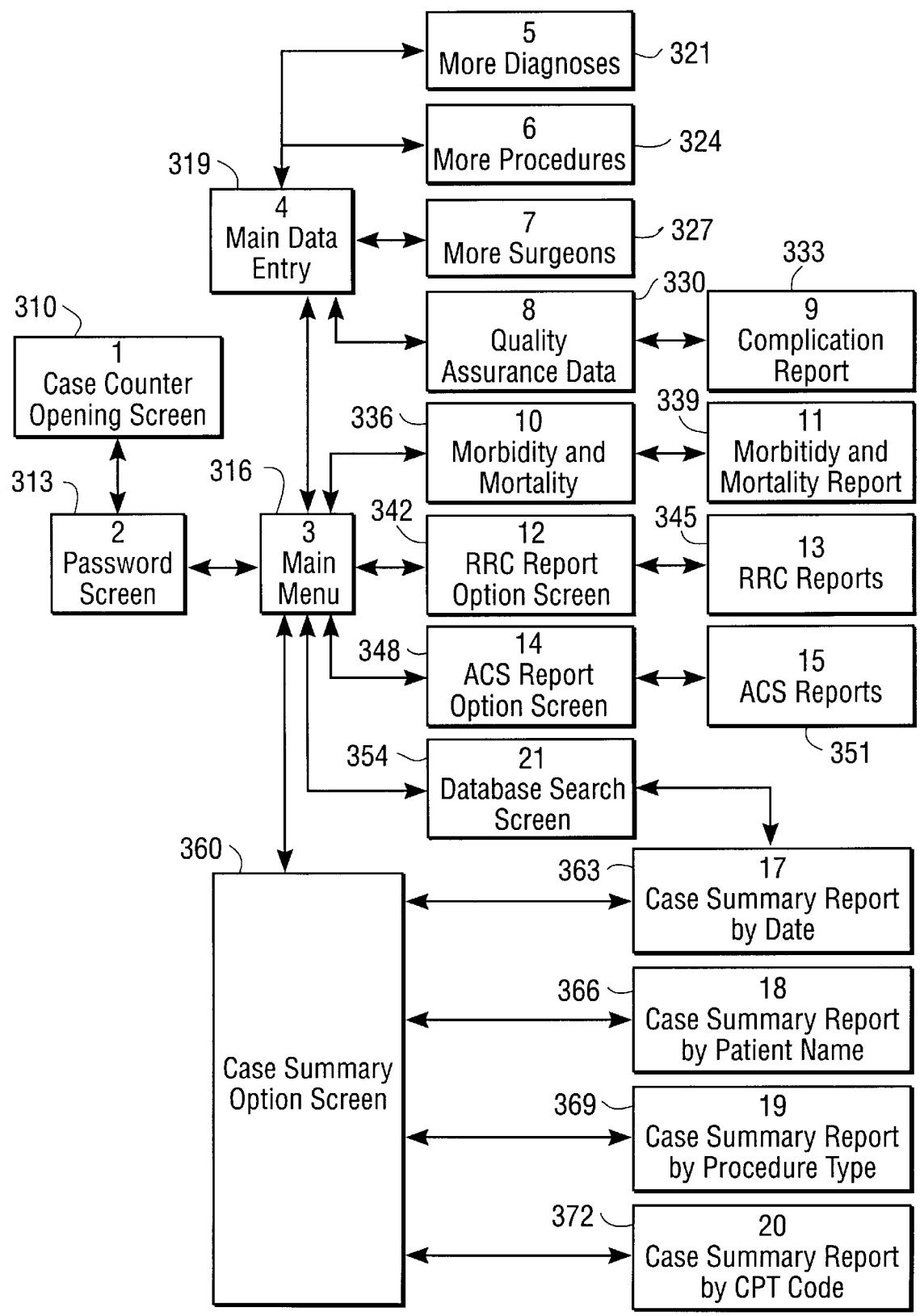
FIG. 3 is a process flowchart for the various functions provided by the computer application.

FIG. 3 is a process flowchart for the various functions provided by the computer application. In the preferred embodiment, there is a correspondence between functions and screens displayed on display device 105, but it is understood that the functions may be organized and implemented in other ways, even without the use of screens. For example, information requesting prompts could be provided to the user on a printer.

When a user begins operative log computer application 202, the first screen displayed on display device 105 is Case Counter Opening Screen 310. From Case Counter Opening Screen 310, The user can choose to proceed to Password Screen 313. At Password Screen 313, if the user types the correct password in response to a prompt, he can proceed to Main Menu 316.

From Main Menu 316, the user can choose to proceed to Main Data Entry Screen 319. At Main Data Entry Screen 319, the user can enter data for each operation. For example, this data can include the following: Patient First Name, Patient Middle Name, Patient Last Name, Patient Initials, Patient Date of Birth, Patient Age, Patient Medical Record Number, Patient Sex, Date of Operation, Outpatient Arrival Indicator, Operative Note Dictated Indicator, Inpatient Indicator, Brief Operative Description, CPT Code, CPT Text Description, RRC Category, RRC CPT Code, RRC Procedure Description, RRC Pediatric/Trauma Indicator, Surgical Program Name, Surgeon Name, Surgeon Post Graduate Year, Surgeon Status, Hospital, Surgical Service, Attending Surgeon First Name, Attending Surgeon Last Name, Patient History, Patient Pre operative Diagnosis, Patient Post Operative Diagnosis, Operative Findings, Pathology, Complication Indicator, Patient Outcome, and Patient Followup. A CPT (Current Procedural Terminology) Code, from this paragraph above, is one procedure from a detailed standard list of procedures. An RRC (Residency Review Committee) Procedure Description, from this paragraph above, is one procedure from the RRC's less-detailed, standard list of procedures. Because the RRC's list of procedures is shorter than the CPT list, certain procedures which would be classified differently in the CPT scheme would be classified as the same under the RRC scheme. The RRC has provided a default one-to-one mapping from each of its procedures into a "corresponding" CPT procedure. This mapping is adequate for many purposes, but for a particular procedure which has been classified into an RRC procedure, the default mapping may not supply the best CPT Code for that procedure. The RRC CPT Code, from this paragraph above, is a datum kept by the computer application to remedy the deficiencies of the RRC mapping. The RRC CPT Code is a CPT Code which the user may enter for an actual procedure, which will override the RRC's default mapping in those places where the RRC's default mapping would otherwise be used, for example, in generating certain reports. An RRC Category is a broad characterization of procedures according to a list of categories chosen by the RRC. In the preferred embodiment, the present invention is used for operations performed by surgeons. The present invention can also be used for any type medical visit involving any type of doctor.

From Main Data Entry Screen 319, the user can choose to proceed to More Diagnoses Screen 321. At More Diagnoses Screen 321, the user can enter diagnoses (e.g., six diagnoses can be entered at one time). For each diagnosis, the user can enter Diagnosis Number, Pre Operative Diagnosis, Post Operative Diagnosis, and ICD9 Code. An ICD9 Code conforms to the International Classification of Disease, 9th Revision. From More Diagnoses Screen 321, the user can return to Main Data Entry Screen 319 or, as a shortcut, proceed directly to More Procedures Screen 324.

From Main Data Entry Screen 319, the user can choose to proceed to More Procedures Screen 324. At More Procedures Screen 324, the user can enter multiple procedures (e.g., six procedures at one time). For each procedure, the user can enter Procedure Number, RRC Procedure Category, RRC Procedure Classification, RRC Procedure Type, RRC CPT Code, Procedure Note, and CPT Code. The RRC Procedure Type is another very broad classification of Procedures defined by the RRC. From More Procedures Screen 324, the user can return to Main Data Entry Screen 319, or as a shortcut, proceed directly to More Diagnoses Screen 321.

From Main Data Entry Screen 319, the user can choose to proceed to More Surgeons Screen 327. At More Surgeons Screen 327, the user can enter surgeons. Data which can be entered at Main Data Entry Screen 319 include Principal Surgeon Name, Additional Surgeon Names (e.g., four additional names may be entered), Procedure Note (e.g., six notes may be added), RRC Coding Matrix (e.g., five Total Surgeons by six Procedures may be entered). From More Surgeons Screen 327, the user can return to Main Data Entry Screen 319.

From Main Data Entry Screen 319, the user can choose to proceed to Quality Assurance Data Screen 330. At Quality Assurance Data Screen 330, the user can enter data related to complication(s), including Type of Complication (e.g., four types may be entered), and Complication Description and Management. The user can also cause to be generated Complication Report 333, which contains data from multiple sources, including those entered in Quality Assurance Data Screen 330 and other screens. The information provided by Complication Report 333 is of the type frequently needed for reports required by hospitals or other organizations. Complication Report 333 may be displayed on display device 105, stored as a file in disk memory 108, or printed by printer 109. From Quality Assurance Data Screen 330, the user can return to Main Data Entry Screen 319.

From Main Data Entry Screen 319, the user can choose to return to Main Menu 316. From Main Menu 316, the user can choose to proceed to Morbidity and Mortality Screen 336. From Morbidity and Mortality Screen 336, the user can cause to be generated Morbidity and Mortality Report 339, which contains statistics related to morbidity and mortality. The information provided by this report is of the type frequently needed for reports required by hospitals or other organizations. The user specifies the set of data for computing statistics by entering restrictions such as Beginning and Ending Dates, Hospital(s), and Surgical Services. Morbidity and Mortality Report 339 may be displayed on display device 105, stored as a file in disk memory 108, or printed by printer 109. From Morbidity and Mortality Screen 336, the user can return to Main Menu 316.

From Main Menu 316, the user can choose to proceed to RRC Report Option Screen 342. From RRC Report Option Screen 342, the user can cause to be generated RRC Report (s) 345, which contain all data required for reporting to the RRC and are of the required layout. These report(s) also contain all data required for reporting to the ABS (American Board of Surgery). The user specifies the type(s) of RRC Report(s) 345 to generate, including those for Major Cases, Minor Cases, Other Major Cases, or Laparoscopic Cases. The user may specify that RRC Report(s) 345 be generated as Hybrid Report(s) With RRC And CPT Codes. Hybrid Reports are based on the RRC layout, but include additional information, including CPT Codes. RRC Report(s) 345 may be displayed on display device 105, stored as a file in disk memory 108, or printed by printer 109. From RRC Report Option Screen 342, the user can return to Main Menu 316.

From Main Menu 316, the user can choose to proceed to ACS Report Option Screen 348. From ACS Report Option Screen 348, the user can cause to be generated ACS Report (s) 351, which contain statistics required for reporting to ACS (American College of Surgeons), including those which make use of ACS's classification scheme for procedures. The user specifies the types of statistics to be included in ACS Report(s) 351, including those for Inpatients or Outpatient Arrivals. RRC Report(s) 345 may be displayed on display device 105, stored as a file in disk memory 108, or printed by printer 109. From ACS Report Option Screen 348, the user can return to Main Menu 316.

From Main Menu 316, the user can choose to proceed to Case Summary Option Screen 360. From Case Summary Option Screen 360, the user can cause to be printed Case Summary Report by Date 363, Case Summary Report by Patient Name 366, Case Summary Report by Procedure Type 369, or Case Summary Report by CPT Code 372. These case summary reports contain summary statistics for each case. The reports differ in the criterion by which cases are sorted into order. The user specifies which type(s) of Case Summary Report is to be printed. These case summary report(s) may be displayed on display device 105, stored as a file in disk memory 108, or printed by printer 109. From Case Summary Option Screen 360, the user can return to Main Menu 316.

From Main Menu 316, the user can choose to proceed to Database Search Screen 354. At this screen, the user can use a multiplicity of selection criteria to specify the cases for which summaries should be produced. The Case Summary Report by Date 363 that is produced has been described above. From Database Search Screen 354, the user can return to Main Menu 316.

Figure 4:
FIG. 4 is an example of a screen display provided by the computer application for data entry.

FIG. 4 is an example of a screen display provided by the computer application for data entry. A screen such as screen display 400 is to be displayed on display device 105 by Main Data Entry Screen 319 as an electronic form whose fields may be filled in or modified by the user 206. To prevent accidental modifications and nonsensical entries, the software application allows certain fields, such as Surgeon Name, to be specially designated so that the software application will not permit the user to change those fields once they have been entered.

FIG. 5 is an example of a screen display for choosing an RRC procedure code during data entry. The user can cause a screen such as screen display 500 to be displayed on display device 105 by Main Data Entry Screen 319, More Procedures Screen 324, or another screen from which RRC codes may be entered by the user. The computer application provides such screens to permit the user to quickly choose the needed RRC procedure code without having to scroll through the entire list of codes. Instead, the computer application: 1) groups procedures according to sections, such as "head and neck"; 2) permits the user to specify the section to which the procedure belongs, by choosing from the small list of all sections; then 3) displays immediately the portion of the list containing RRC codes for procedures belonging to that section; and 4) permits the user to select one of the RRC codes displayed. If the user does not know the section, the computer application will permit the default mode of scrolling through the entire list of procedures.

Figure 6A:
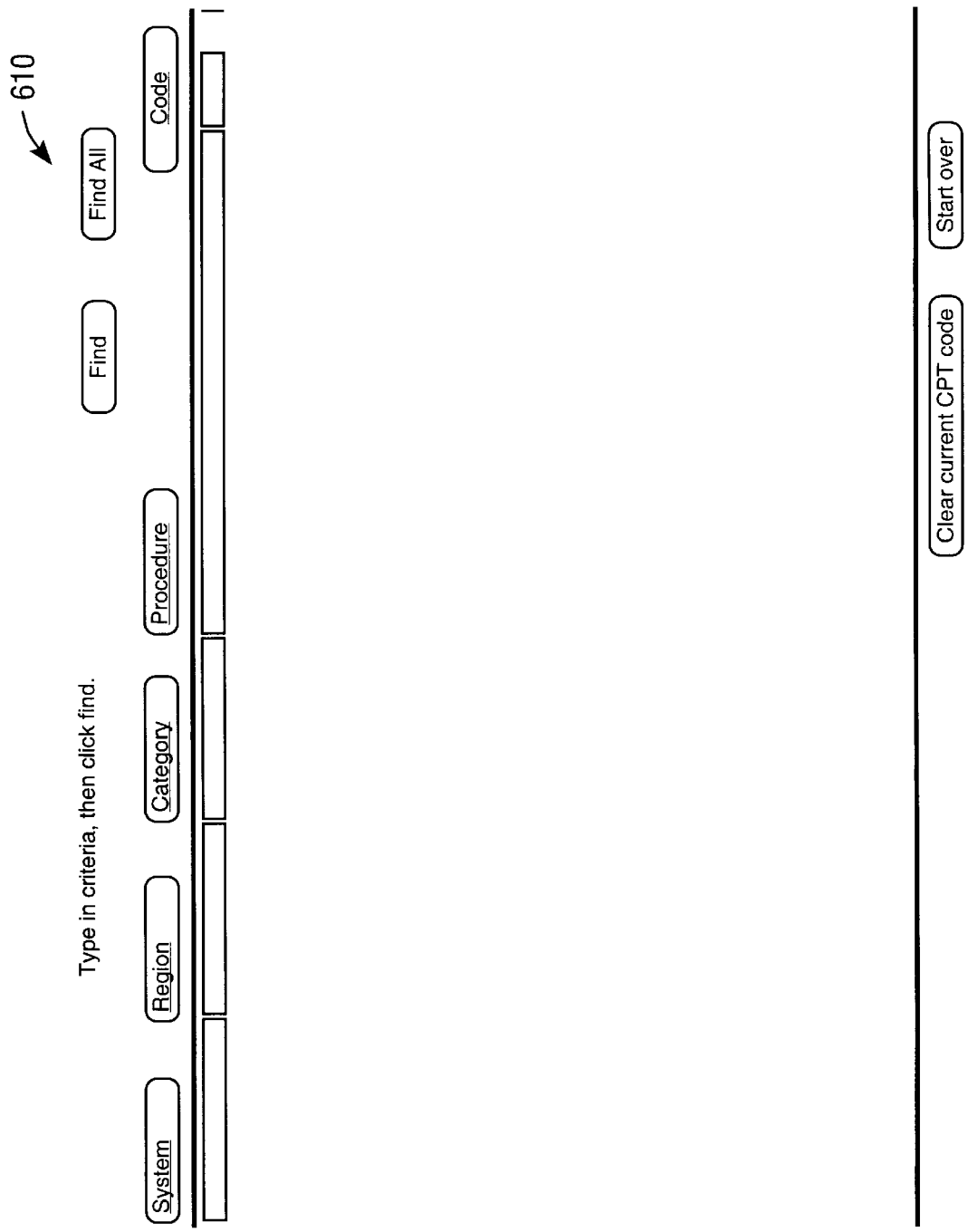

FIGS. 6A–D are examples of screen displays for finding a CPT procedure code during data entry. In the preferred embodiment, screens such as those in FIGS. 6A–D are displayed on display device 105 by Main Data Entry Screen 319, More Procedures Screen 324, or another screen from which CPT codes may be entered by the user. The computer application provides such screens to permit the user to quickly find the needed CPT procedure code from a large list. The user is not forced to scroll through the entire list of thousands of CPT codes. Instead, the computer application uses the AMA's (American Medical Association's) classification of CPT procedure codes according to four variables: system, region, category, and procedure. The user can specify those variables of the needed CPT code that the user knows, by choosing from small lists of all systems, all regions, all categories, and all procedures. Thereafter, the computer application will display the list of matching CPT procedure codes, from which the user can pick the desired one. Screen 610 in FIG. 6A is an example of a screen from which the user can specify the known variables of the needed CPT code. In addition to specifying known variables, the user can also enter directly to Screen 610 a CPT procedure code or a range of CPT procedure codes. Thereafter, the computer application will display the list of matching CPT procedure code(s) and their variables, from which the user can pick the desired one, or confirm that the one he picked was correct now that he sees its informative variables. Screen 620 in FIG. 6B is an example of a screen in which the user has specified directly a CPT procedure code and caused the computer application to display that procedure's informative variables so that the user can confirm it. Screen 630 in FIG. 6C is an example of a screen in which the user has specified directly a range of CPT procedure codes and caused the computer application to display CPT procedure codes within that range so that the user may choose one. Screen 640 in FIG. 6D is another example of a screen in which a user has specified directly a range of CPT procedure codes. Screen 640 also allows the user to narrow the list of operations by checking a box in preferred column 650. Thus, the user can mark a box in preferred column 650 such that the most frequent operations are listed first within screen 640.

Figure 7:
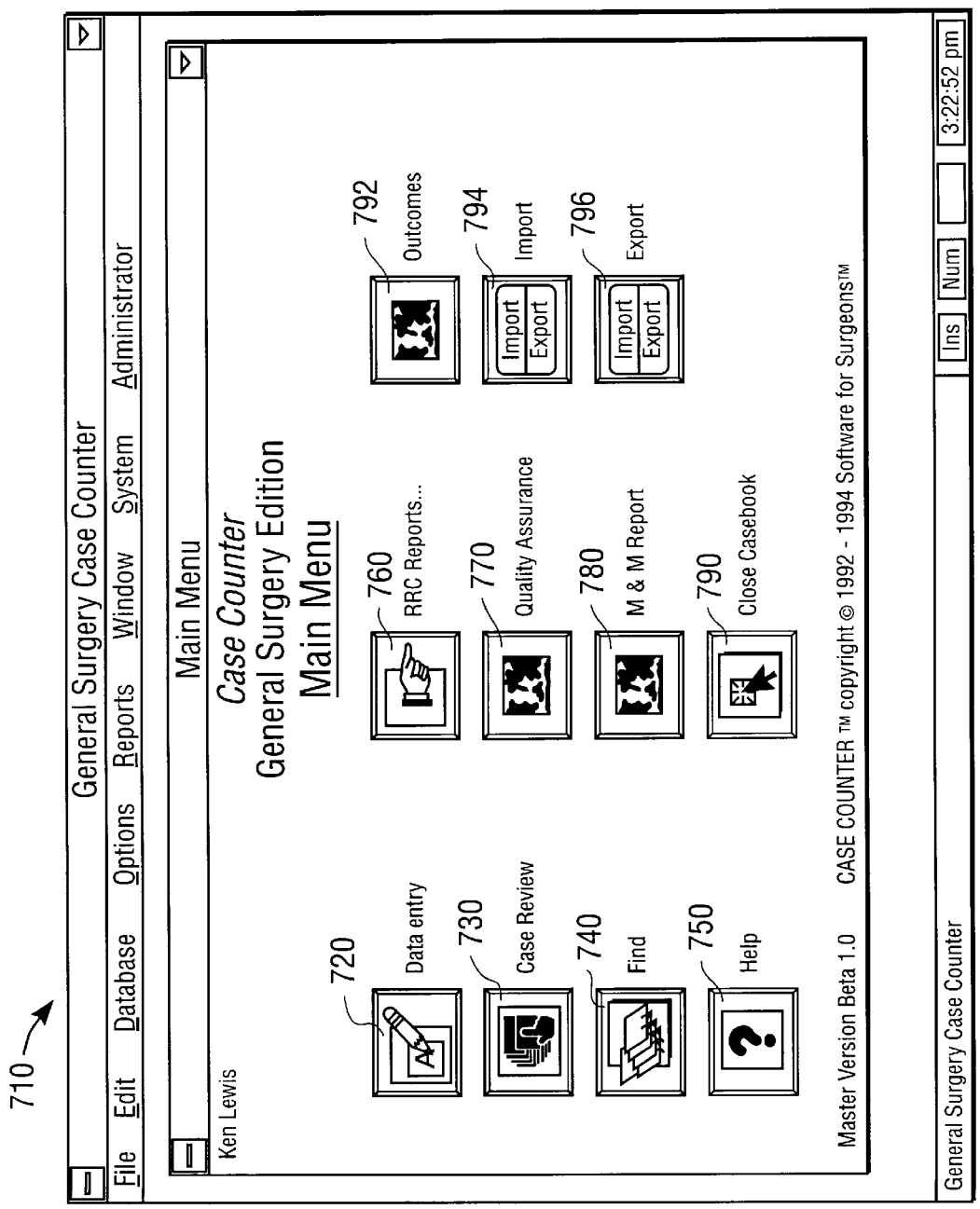
FIG. 7 is an example of the main menu screen display.
Figure 8:
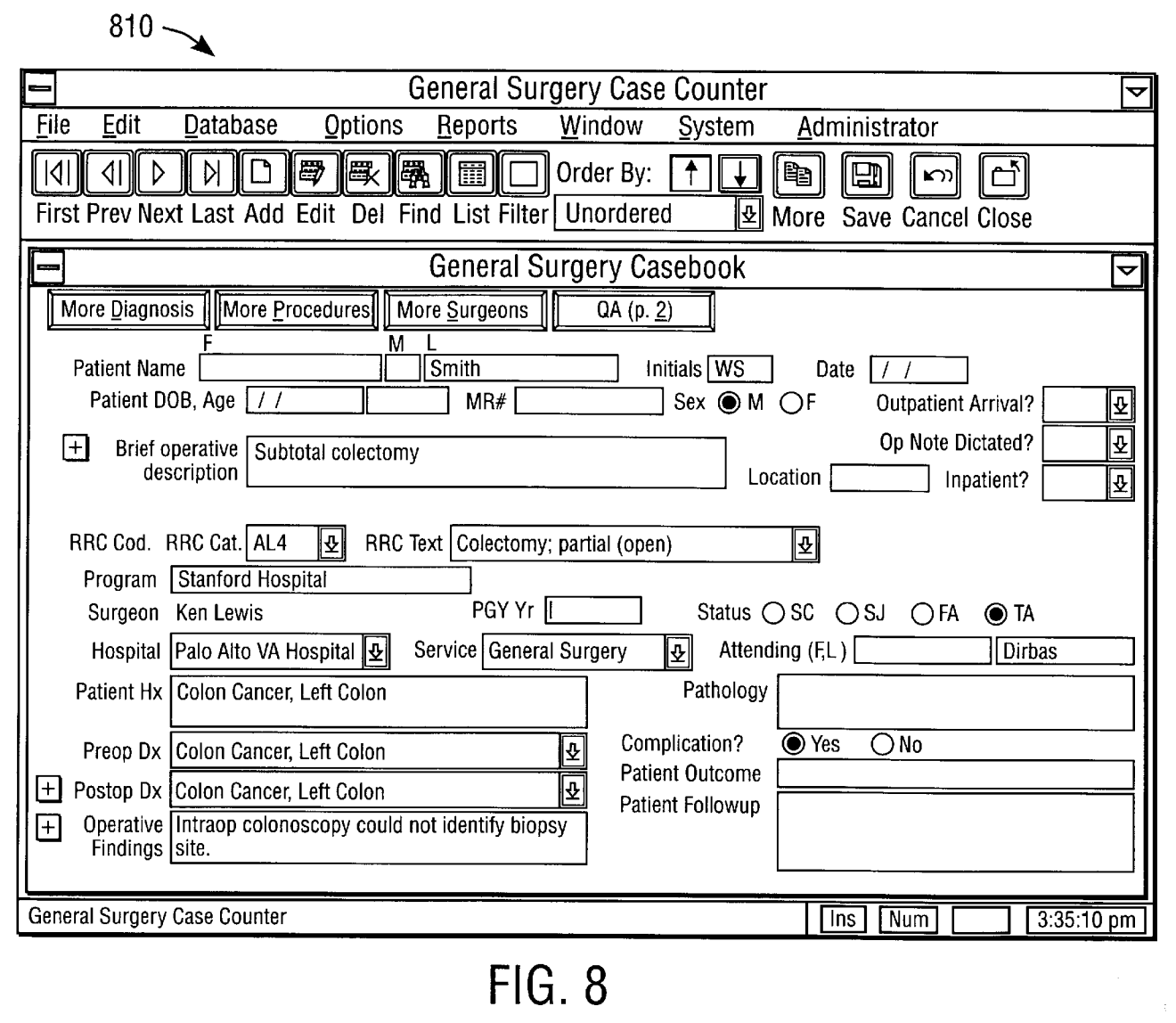

FIG. 7 is an example of the main menu screen display, which is Main Menu Screen 316 in FIG. 3. In the preferred embodiment, main menu screen display 710 is a standard Window display which includes icons for Data Entry 720, Case Review 730, Find 740, Help 750, RRC Reports 760, Quality Assurance 770, M&M Report 780, Close Casebook 790, Outcomes 792, Import 794, and Export 796. FIG. 8 is an example of the main data entry screen display, which is Main Data Entry Screen 319 in FIG. 3. As described above, various data related to a medical visit/procedure is entered via main data entry screen 810.

Figure 9A:
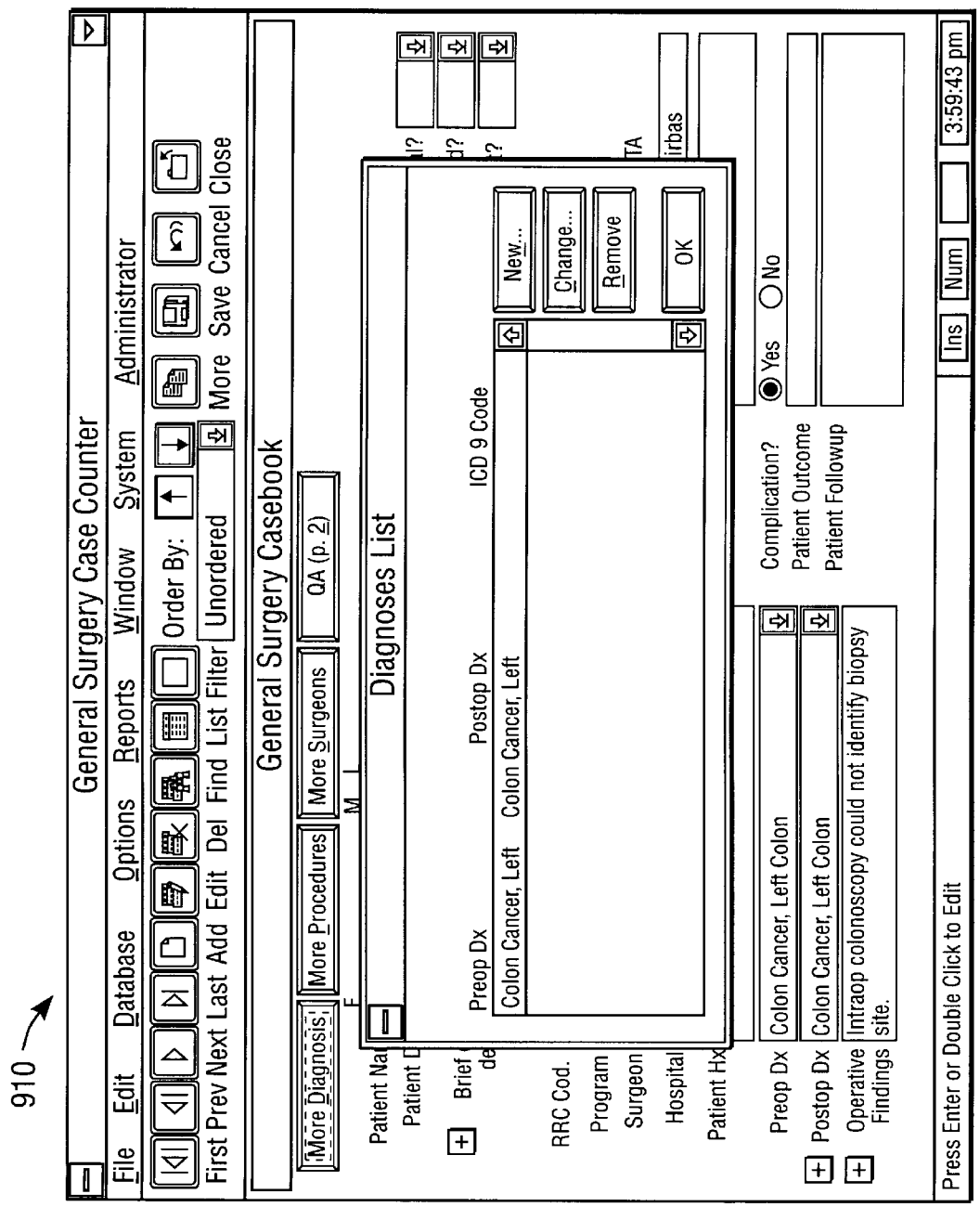
FIG. 9A is an example of a screen display for entering more diagnoses.
Figure 9B:
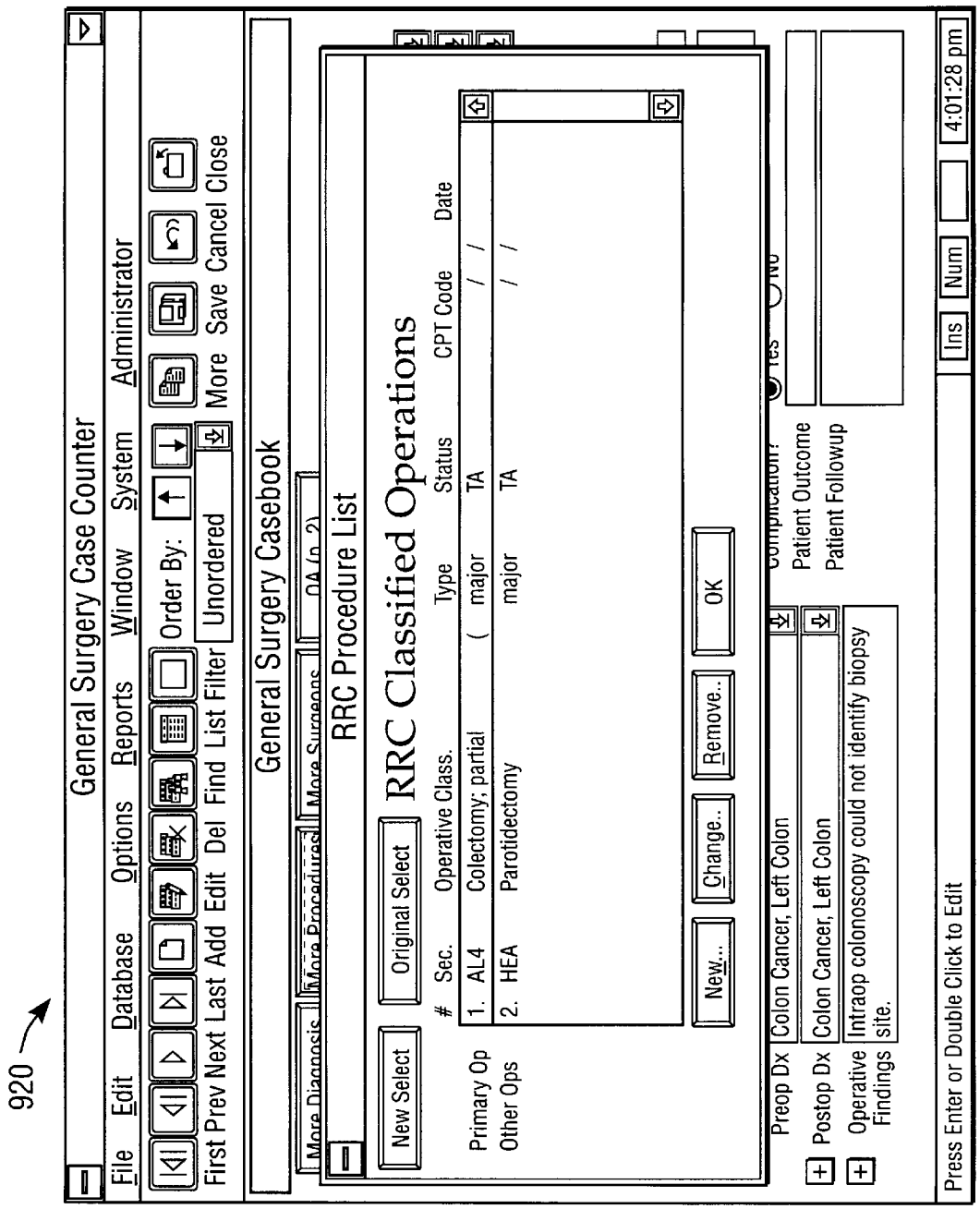
FIG. 9B is an example of a screen display for entering more procedures.

FIG. 9A is an example of a screen display for entering more diagnoses, which is More Diagnoses Screen 321 in FIG. 3. In the preferred embodiment, this screen display 910 is an overlay on the main data entry screen as shown in FIG. 9A. FIG. 9B is an example of a screen display for entering more procedures, which is More Procedures Screen 324 in FIG. 3. In the preferred embodiment, this screen display 920 is also an overlay on the main data entry screen as shown in FIG. 9B.

Figure 10:
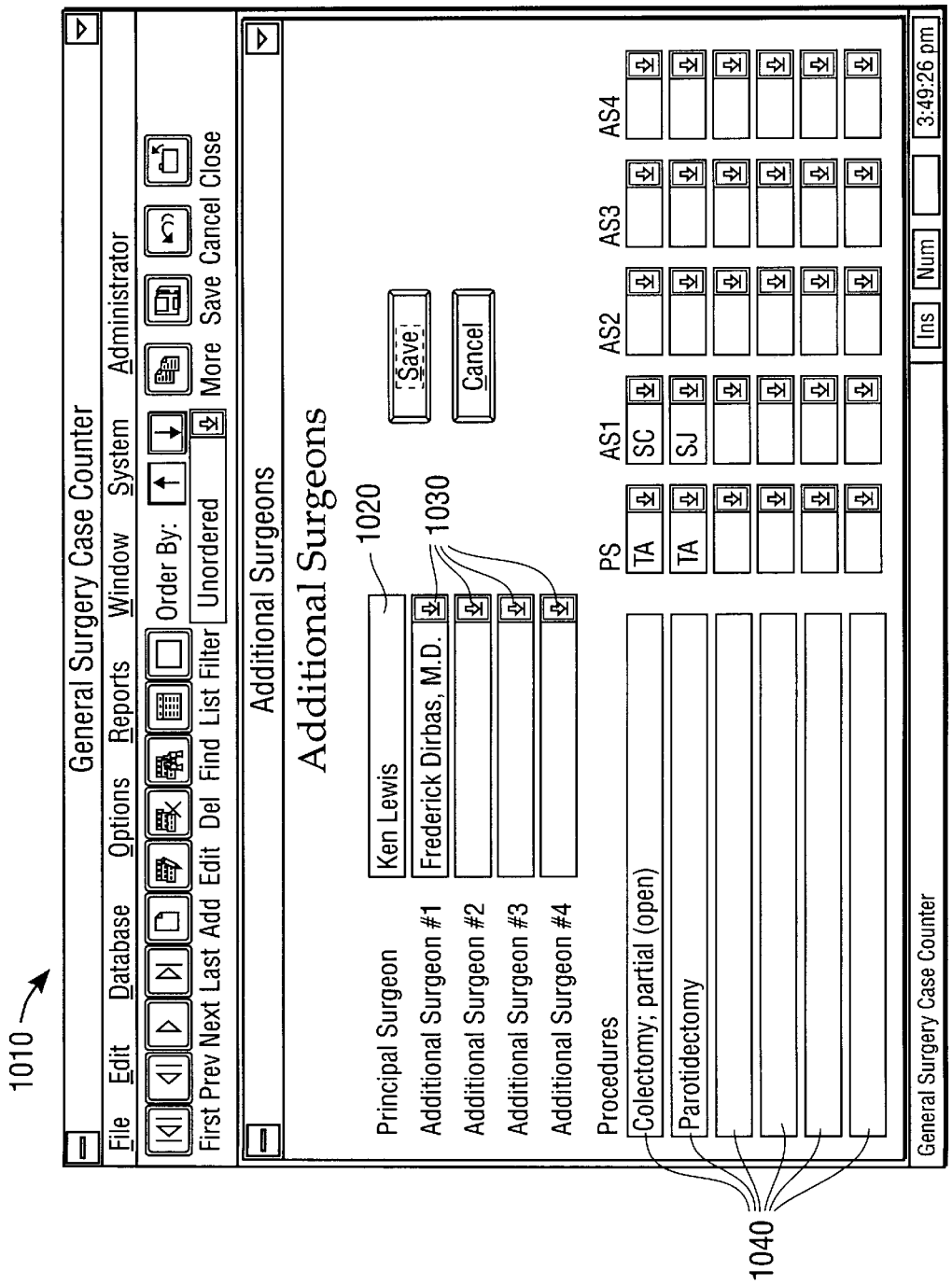
FIG. 10 is an example of a screen display for entering more surgeons.

FIG. 10 is an example of a screen display for entering more surgeons, which is More Surgeons Screen 327 in FIG. 3. In the preferred embodiment, this screen display 1010 has data entry spaces for a principal surgeon 1020, additional surgeons 1030, multiple procedures 1040, etc.

Figure 11A:
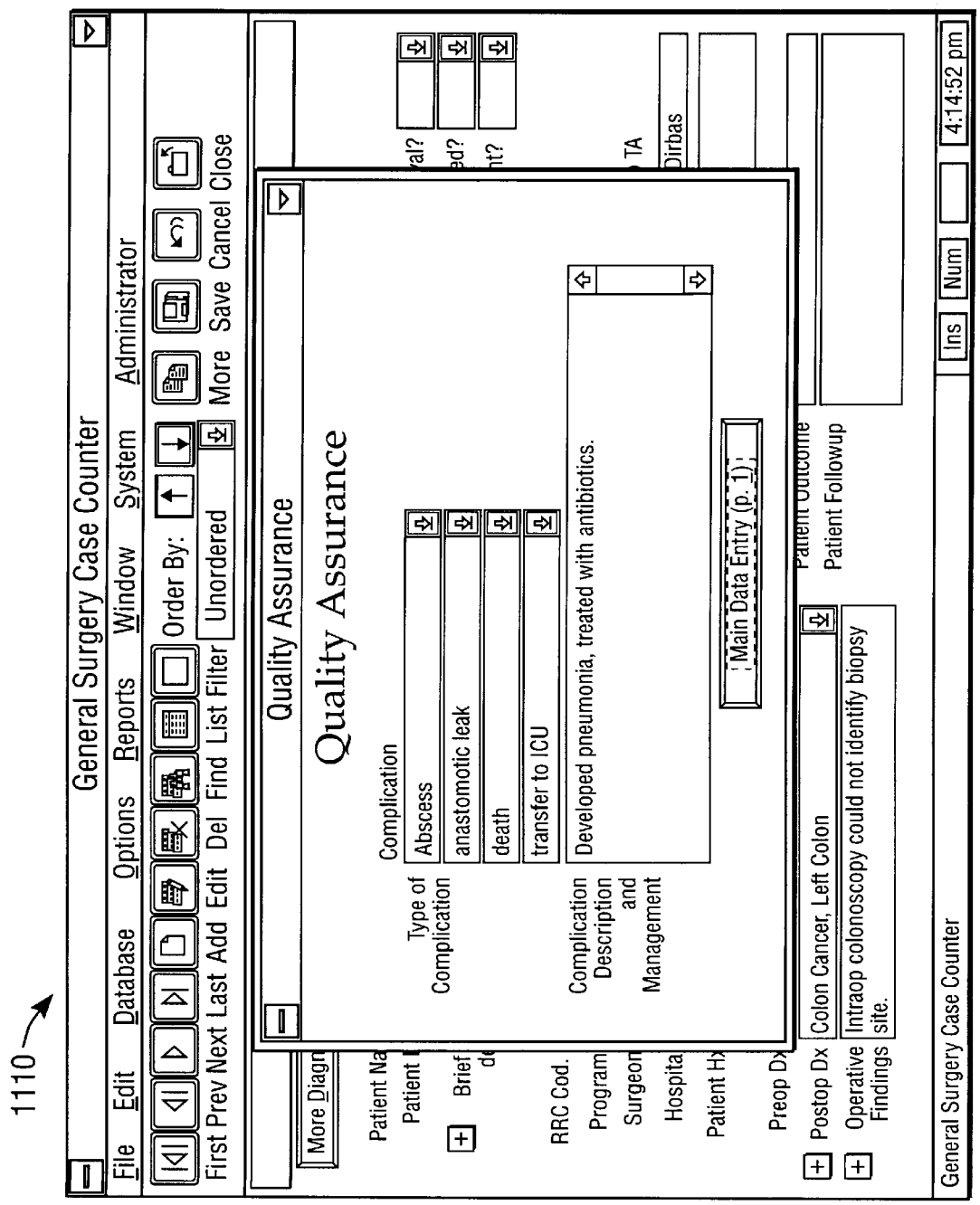
FIG. 11A is an example of a screen display for entering quality assurance data.
Figure 11B:
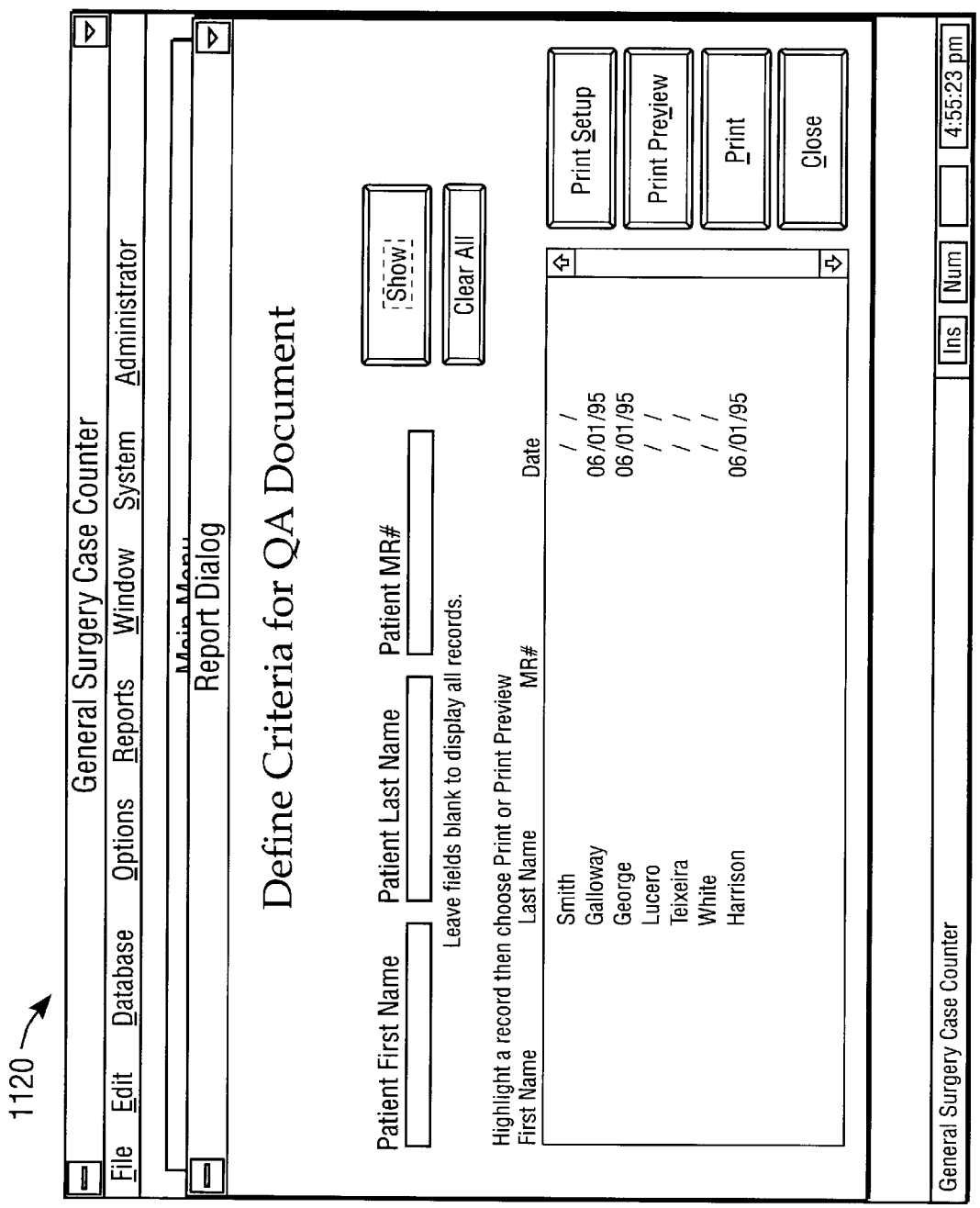
FIG. 11B is an example of a screen display for selecting the data to include in a complication report.

FIG. 11A is an example of a screen display for entering quality assurance data, which is More Procedures Screen 324 in FIG. 3. This screen display 1110 can contain complication information. FIG. 11B is an example of a screen display 1120 for selecting the data to include in a complication report, which is Quality Assurance Data Screen 330 in FIG. 3.

Figure 12:
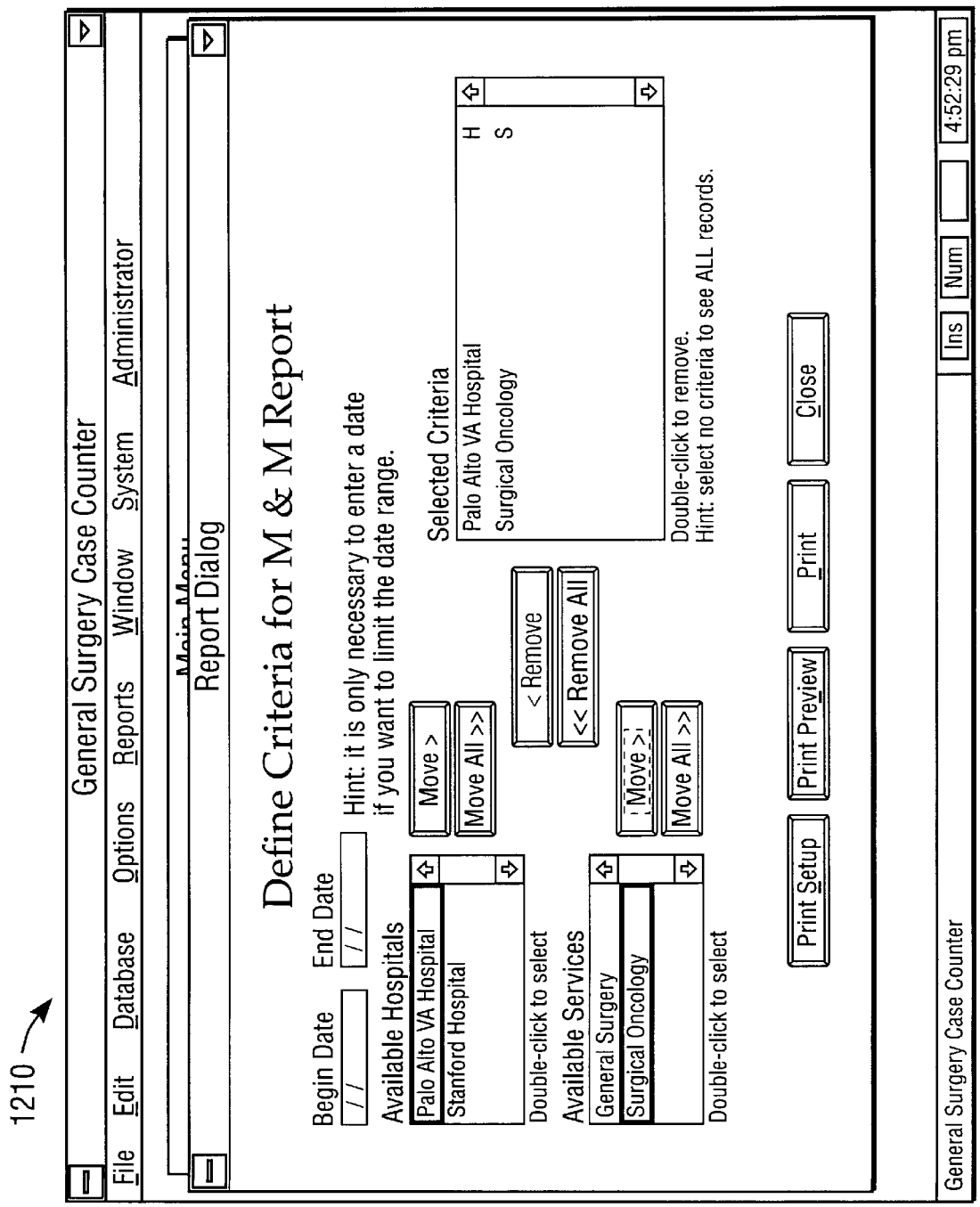
FIG. 12 is an example of a screen display for selecting the data to include in a morbidity and mortality report.
Figure 13:
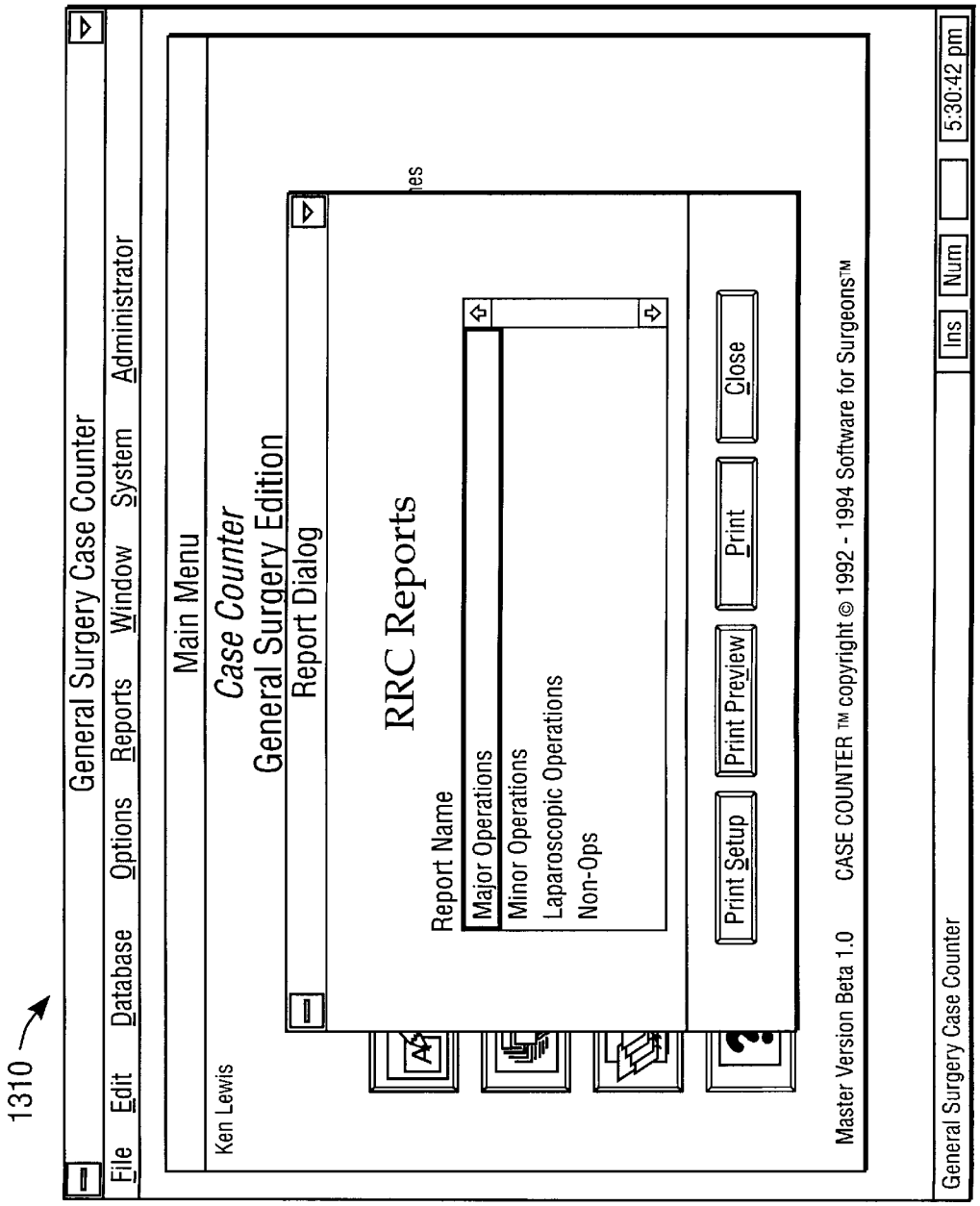
FIG. 13 is an example of a screen display for selecting the data to include in an RRC report.

FIG. 12 is an example of a screen display 1210 for selecting the data to include in a morbidity and mortality report, which is generated by Quality Assurance Data Screen 330 in FIG. 3. FIG. 13 is an example of a screen display 1310 for selecting the data to include in an RRC report, which is generated by RRC Report Option Screen 342 in FIG. 3. FIG. 14 is an example of a screen display 1410 of a case summary report by date, which is Case Summary Report by Date 363 in FIG. 3.

Figure 15:
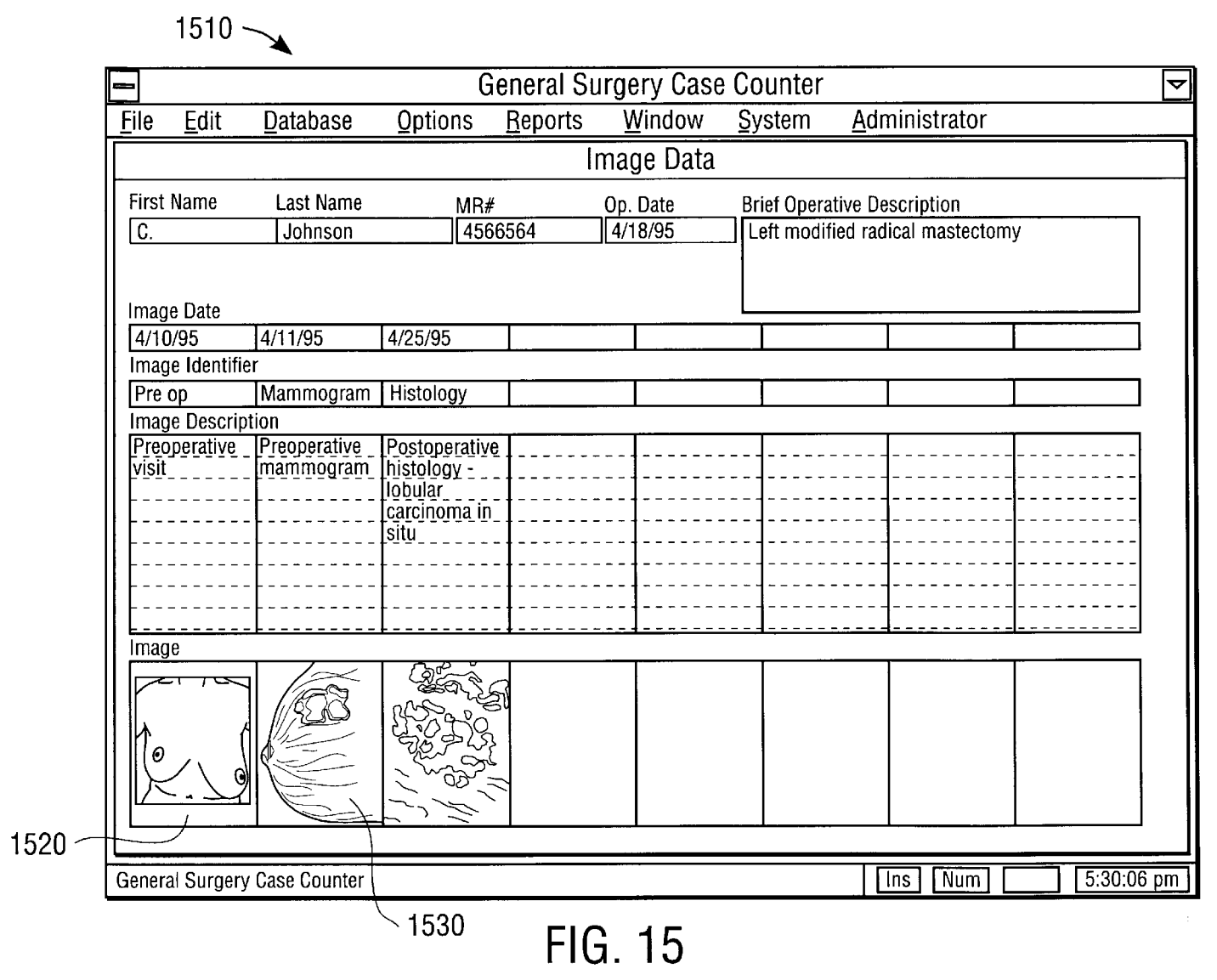

FIG. 15 is an example of a screen display for entering and retrieving image data. For example, a photograph can be scanned and converted into image 1520. Digital pictures and video inserts can also be entered as an image such as image 1520, or as a video field within screen display 1510. In addition, data from complex medical scanning/monitoring devices can be used to generate image 1530. Image data screen 1510 contains patient information, operation information, and related image information.

In the preferred embodiment, the software program used to provide the medical information log system of the present invention is organized around the various available screen displays. Software assisting programs can be used to implement this software program. For example, in the preferred embodiment, the FoxPro version of this software program uses a software assistance program entitled FoxExpress from Neon Software. FoxExpress can, for example, automate standard buttons within the available screen displays.

Furthermore, the software program of the present invention can be utilized to provide medical log information to a large group of users. For example, entered medical log information can be accessible to users over a network. Additionally, disks (e.g., floppy disks, CDs and the like) with medical log information can be sent to users. These disks can contain a full database of information or they can contain updates for an already present medical log database. When updates are provided, an additional software program is used to assist in the updating of changed/additional information in the medical log database.

Additionally, software located on a disk (e.g., floppy disks, CDs and the like) can be used to extract data from a user's local database. For example, a hospital, which is not networked with a larger group of system users, can build up their own internal database with medical visit data. External system users could then retrieve data from the hospital's local database by sending the hospital a disk with the extracting software. After this disk is inserted into a disk drive in a computer having access to the local database, the extracting software first searches the database for the desired data and then copies that data into a smaller database constructed on the extracting disk. The disk can then be sent to the external system user for data retrieval. Thus, the searching and storing is done by software on a disk, so the hospital system users do not have to perform this task.

Figure 16:
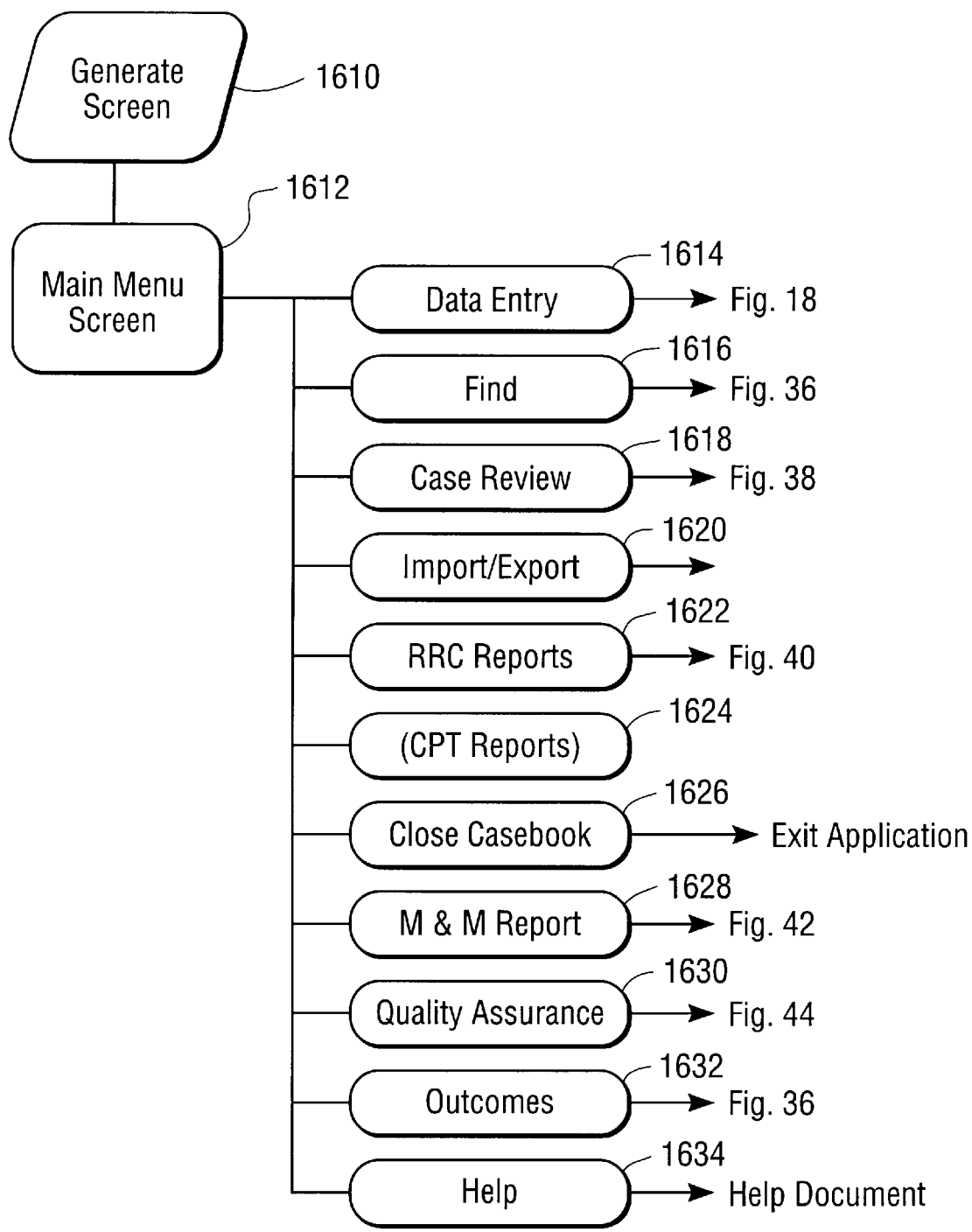
FIG. 16 is a process flow chart associated with the main menu screen.
Figure 17:
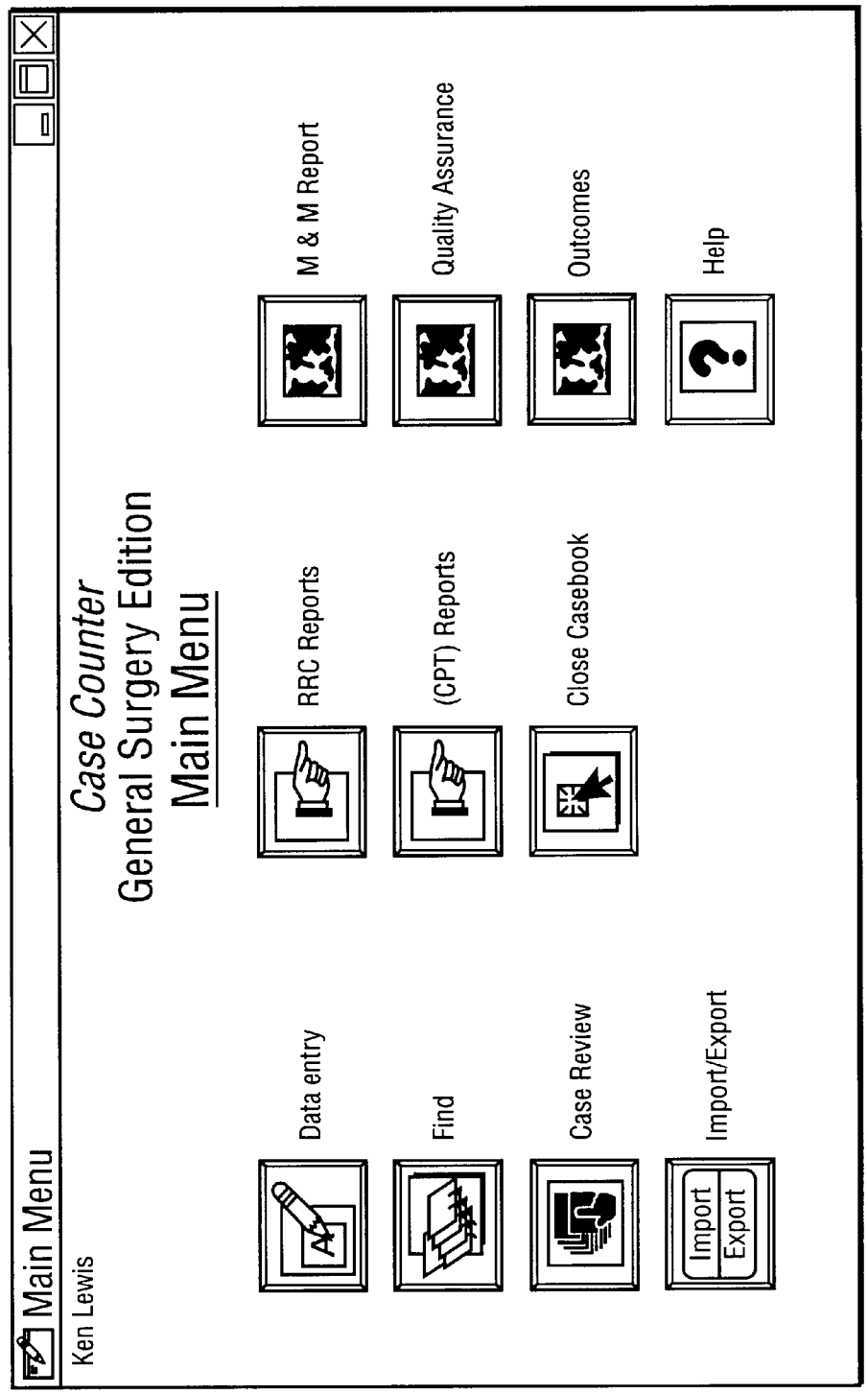
FIG. 17 is another example of the main menu screen display.

FIG. 16 is a process flow chart associated with the main menu screen. At step 1610, the main menu screen is generated. The main menu screen is then displayed at step 1612. FIG. 17 is another example of the main menu screen display. After the main menu screen 1710 is displayed, a user can choose to proceed to any of the available features by selecting one of the displayed icons. In this example, the available features include the following: data entry, find, case review, import/export, RRC reports, CPT reports, close casebook, Morbidity and Mortality (M and M) report, quality assurance, outcomes, and help. As shown in FIG. 16, each of these features utilizes a separate part of the software program in the preferred embodiment.

Figure 18:
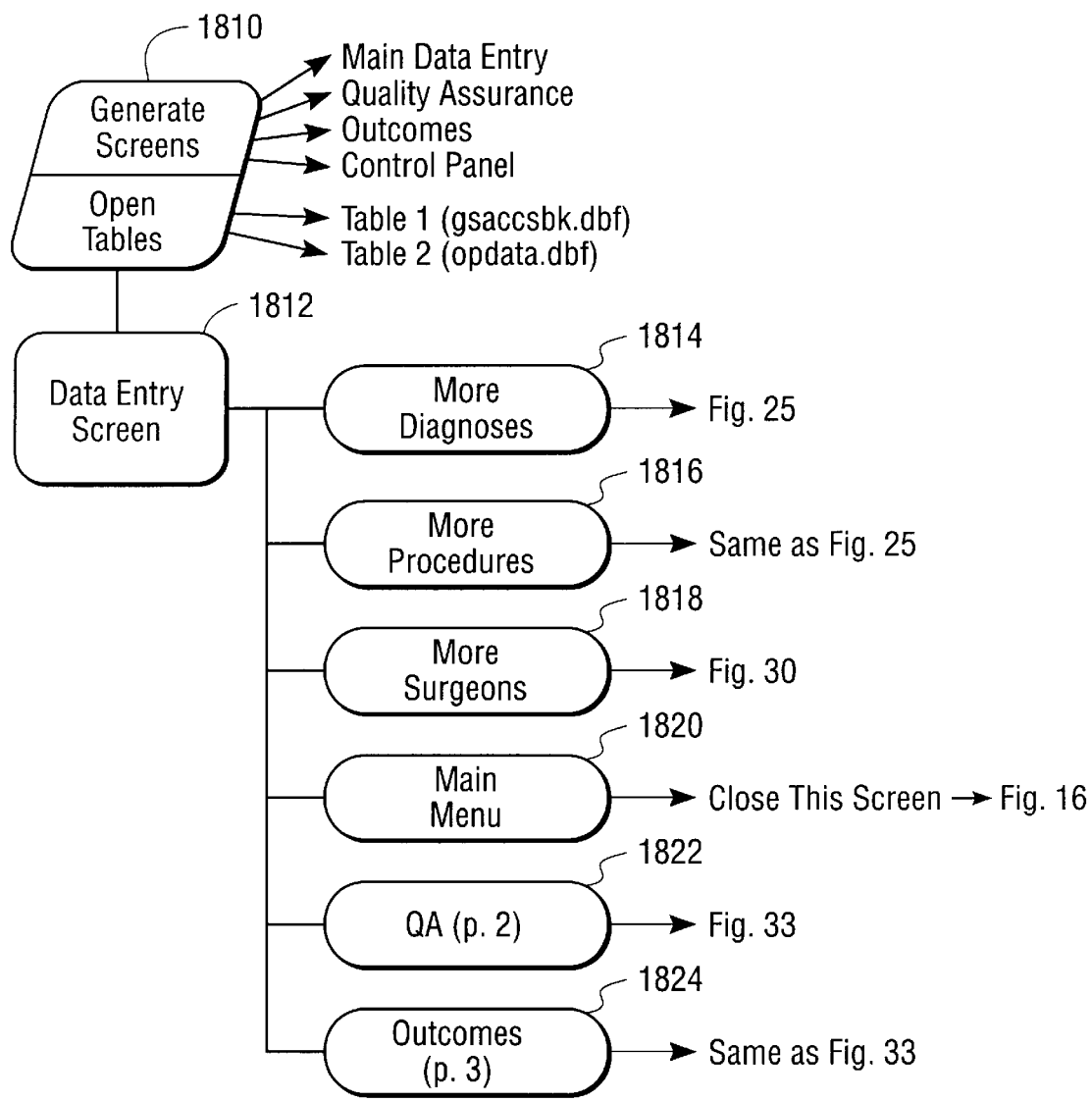
FIG. 18 is a process flow chart associated with the data entry screen.
Figure 19:
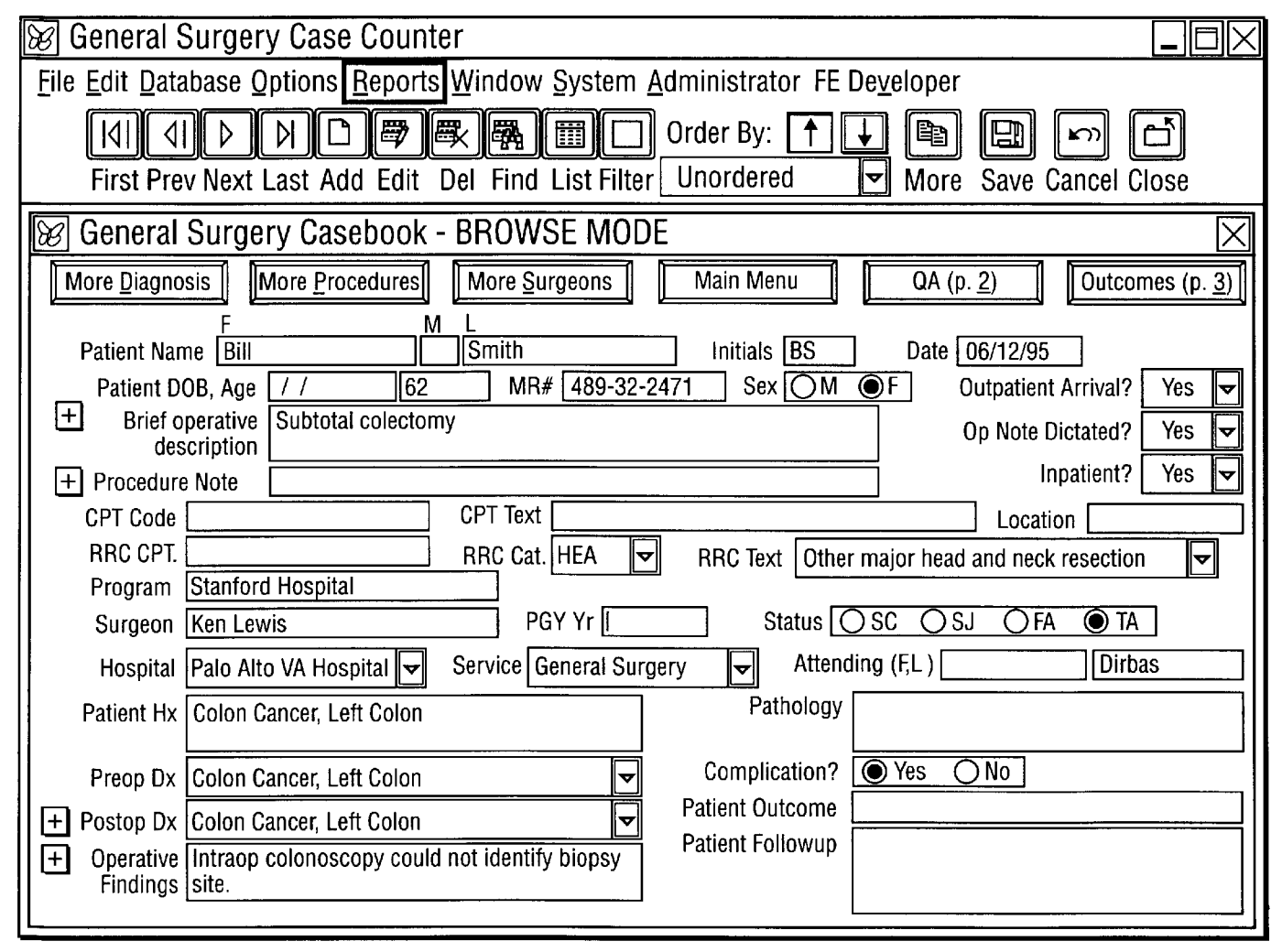
Figure 20:
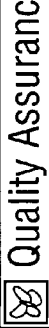
FIG. 20 is another example of a quality assurance screen display.
Figure 22:
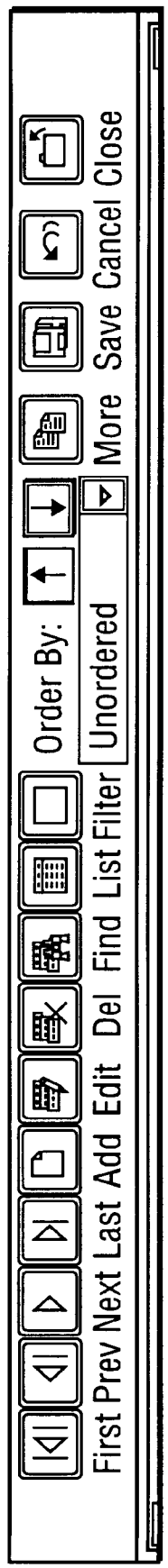
FIG. 22 is an example of a control panel screen display which assists a user in navigating through the software and making edits to data entries.

FIG. 18 is a process flow chart associated with the data entry screen. When the data entry feature is selected by a user at step 1614 (see FIG. 16), main menu screen 1612 is closed and the process flow chart in FIG. 18 begins. At step 1810, several screens are generated and two tables are opened. The screens include, for example, a main data entry screen, a quality assurance screen, an outcome screen, and a control panel screen. The tables include Table 1 and Table 2. FIG. 19 is another example of a screen display for entering main data. This screen is described in greater detail above. FIG. 20 is another example of a quality assurance screen display. The quality assurance screen can, for example, contain data fields for the following: type of complication, and complication description and management. FIG. 21 is an example of a screen display for entering outcomes data. outcomes data can, for example, include the following: follow-up information, outcome information, data of last contact, date of next appointment, and death related information. FIG. 22 is an example of a control panel screen display which assists a user in navigating through the software and making edits to data entries.

FIG. 23 is an example of Table 1 which includes the information associated with the fields listed under the Field Name column (e.g., CASEID, CASEDATE, PATFNAME, PATMNAME, PATLNAME, etc.). FIG. 24 an example of Table 2 which includes information related to the fields included under the Field Name column (e.g., OPDATAID, CASEID, OPERID, CASEOPID, etc.). These tables are used to organize and track entered data.

Now turning back to FIG. 18, after the screens are generated and tables are opened at step 1810, a data entry screen (shown in FIG. 19) is displayed at step 1812. From the data entry screen, the user can select yet another feature of the program such as more diagnosis, more procedures, more surgeons, main menu, quality assurance, and outcome.

Figure 25:
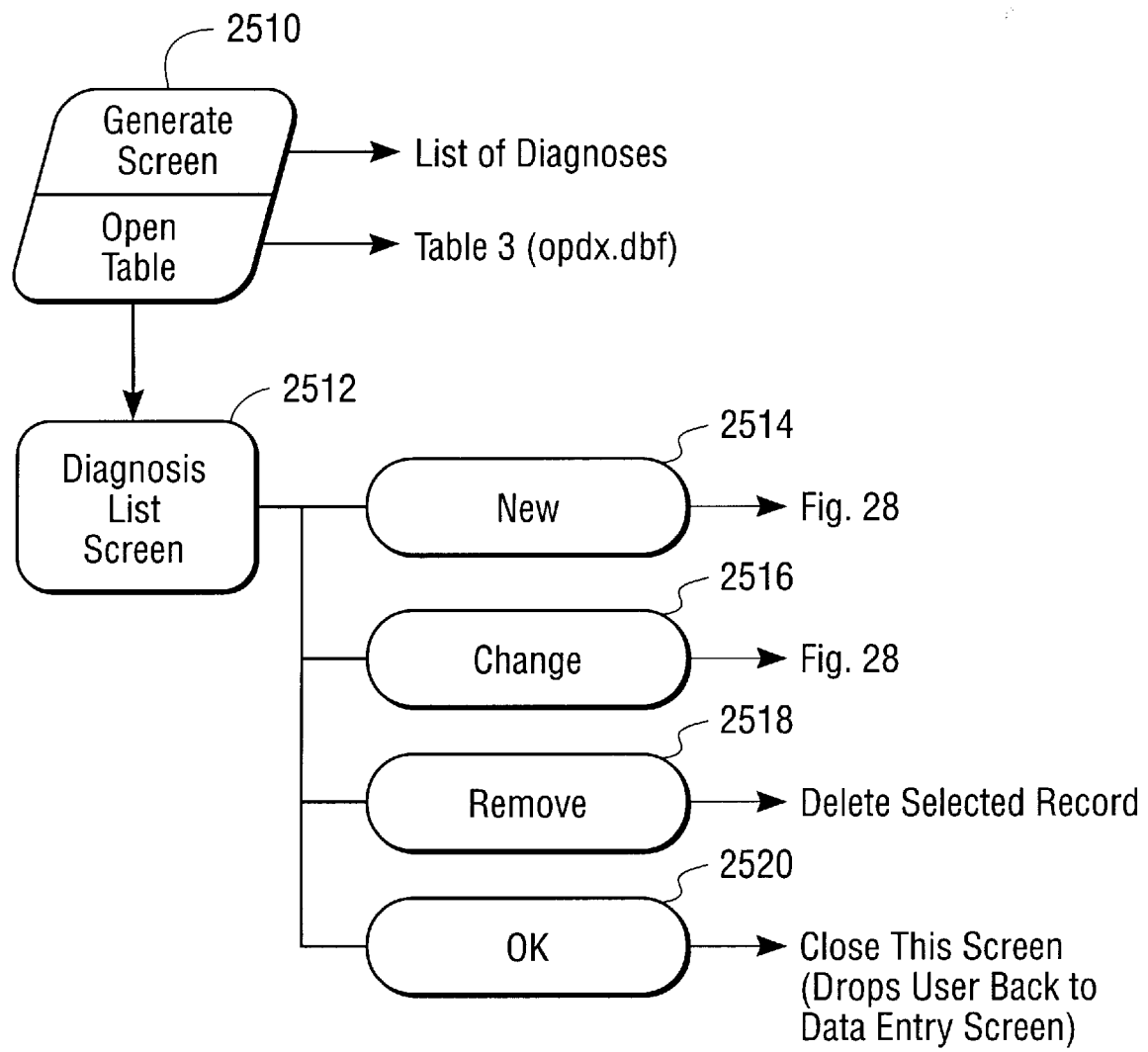
FIG. 25 is a process flow chart associated with the more diagnosis feature.
Figure 26:
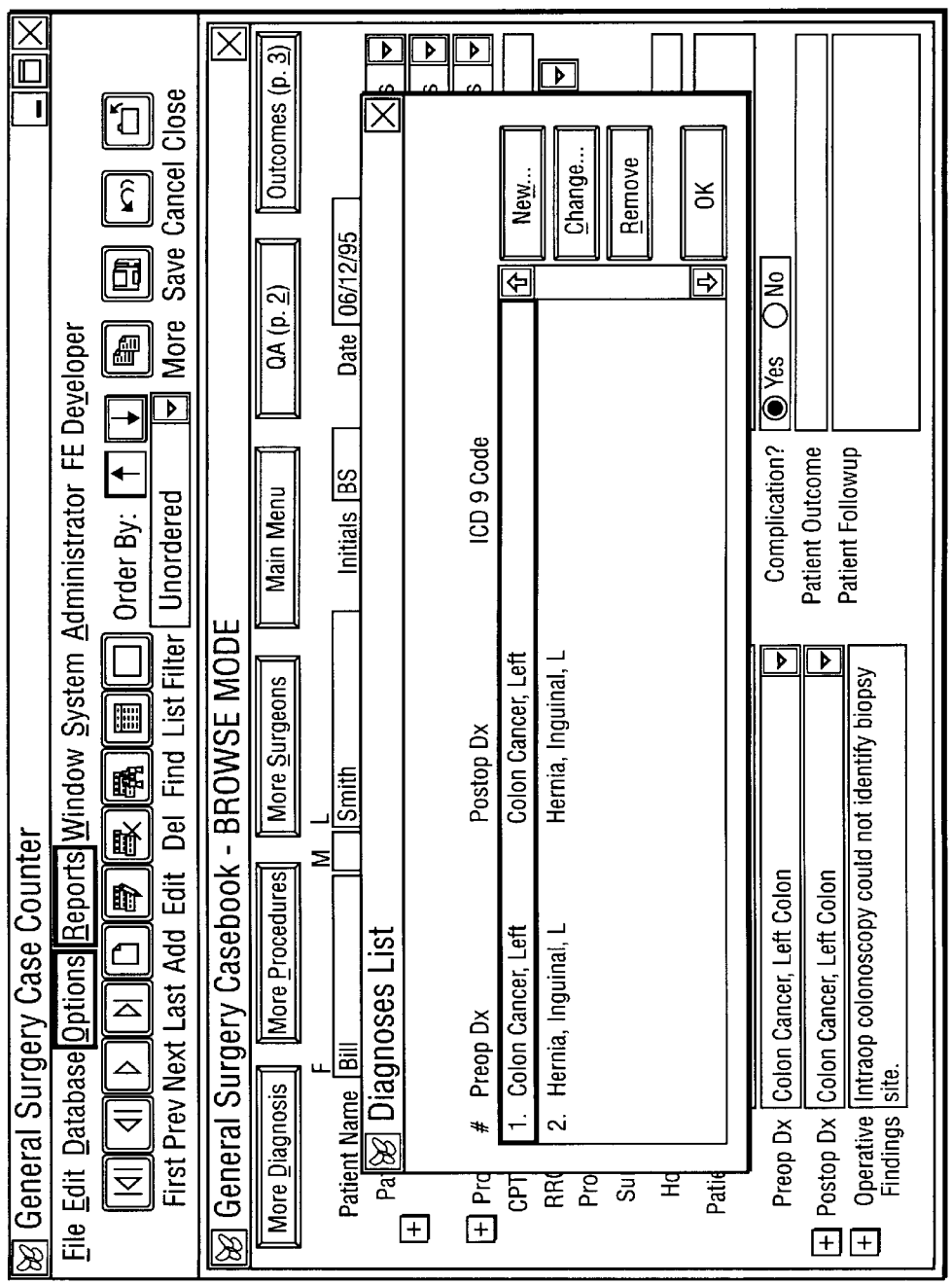
FIG. 26 is an example of a screen display for a list of diagnoses.
Figures 27, 28:
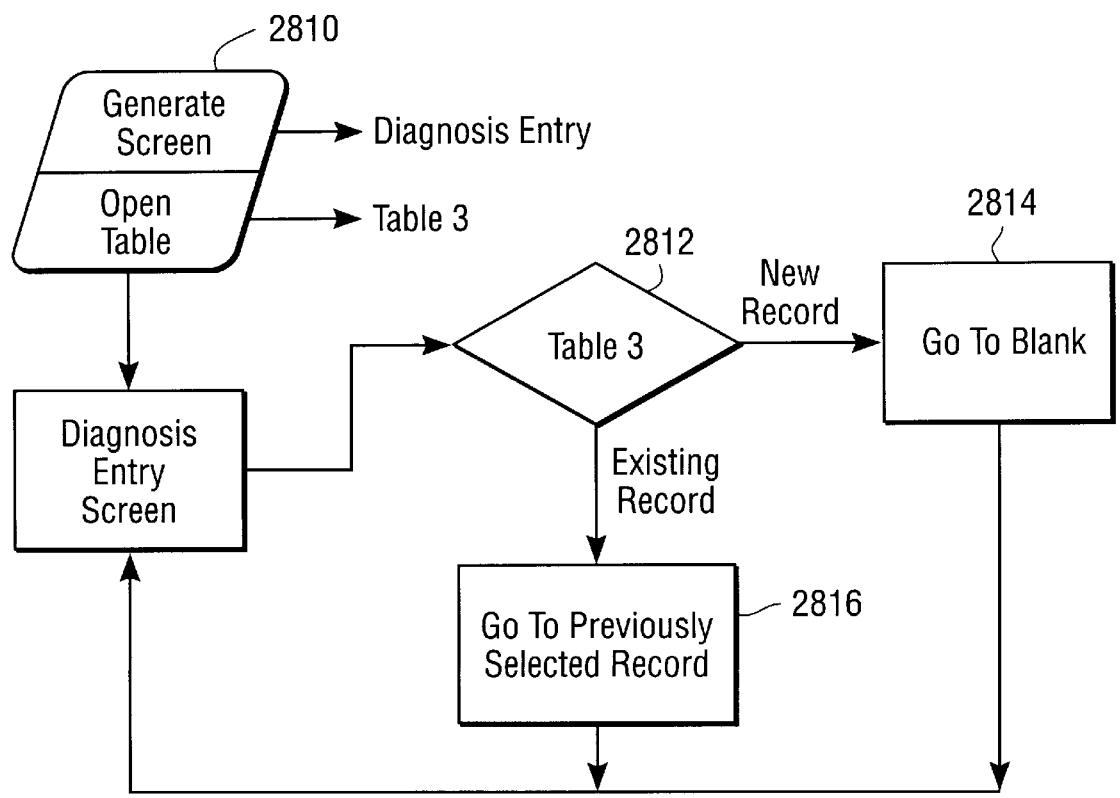
FIG. 27 is an example of Table 3 which includes information related to the fields listed in the Field Name column (e.g., CASEID, CASEDXID, PREOPDX, etc.)
FIG. 28 is a process flow chart for entering diagnosis information.
Figure 29:
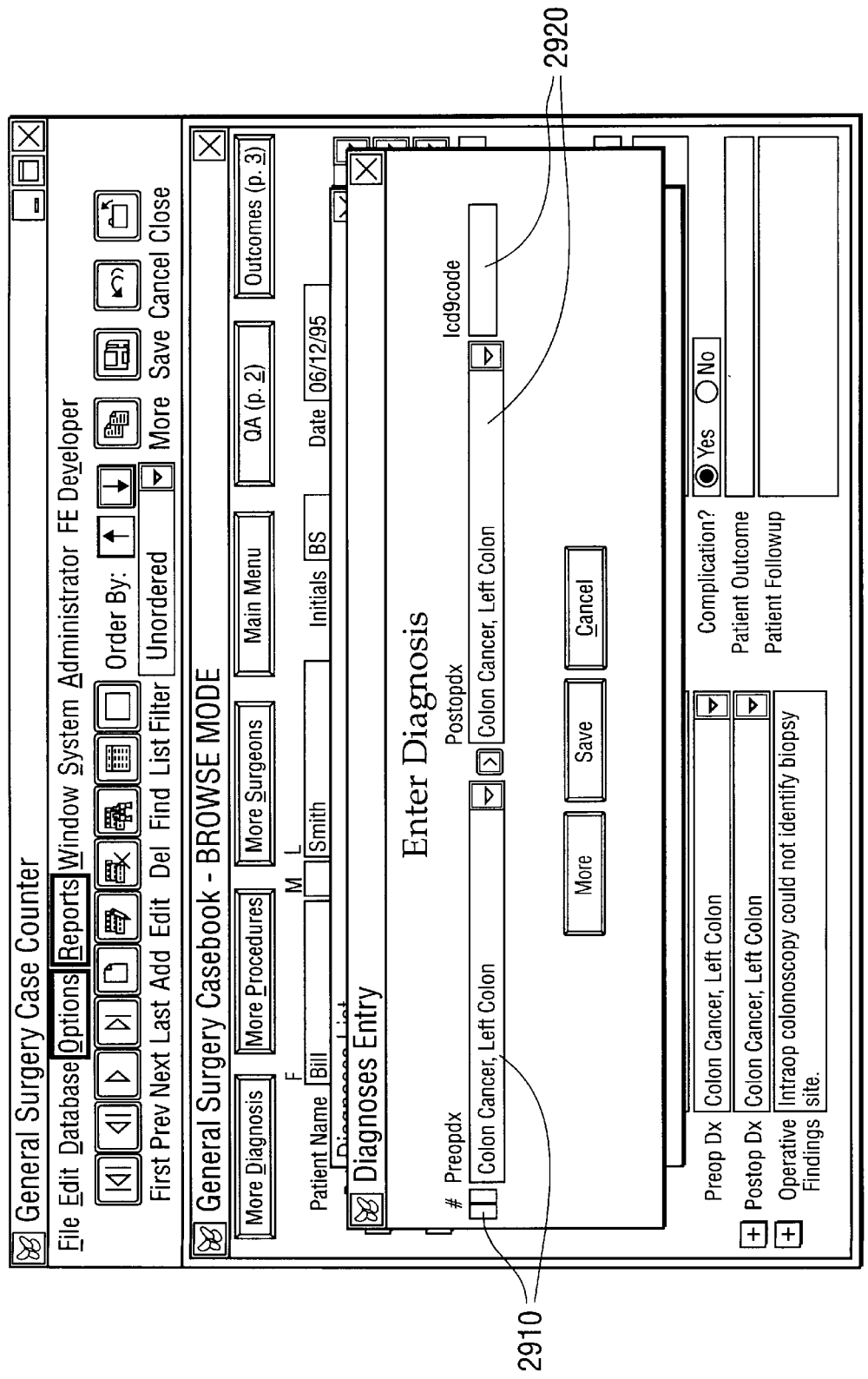
FIG. 29 is an example of a screen display for entering diagnoses.

FIG. 25 is a process flow chart associated with the more diagnosis feature. When a user selects more diagnosis at step 1814 (see FIG. 18), a list of diagnoses screen is generated and Table 3 is opened at step 2510. FIG. 26 is an example of a screen display for a list of diagnoses. In the preferred embodiment, the diagnosis list screen is an overlay on the data entry screen as shown in FIG. 26. FIG. 27 is an example of Table 3 which includes information related to the fields listed in the Field Name column (e.g., CASEID, CASEDXID, PREOPDX, etc.). At step 2512, the diagnosis list screen shown in FIG. 26 is displayed on display device 105. The user can then select (1) to enter a new diagnosis at step 2514, (2) to change a diagnosis entry at step 2516, (3) to remove a diagnosis list record at step 2518, or (4) to close the screen by selecting OK at step 2520. When an entry in the diagnosis list is removed at step 2518, the selected record is deleted from Table 3. When a user selects to close the screen by selecting OK at step 2520, the user is returned to the data entry screen at step 1812 in FIG. 18. FIG. 28 is a process flow chart for entering diagnosis information. This process flowchart occurs when a user selects (1) to enter a new diagnosis at step 2514, or (2) to change a diagnosis entry at step 2516. At step 2810, the diagnosis entry screen is generated and Table 3 is opened again. FIG. 29 is an example of a screen display for entering diagnoses. In the preferred embodiment, the enter diagnosis screen is an overlay as shown in FIG. 29. The user can then enter diagnosis information within displayed fields 2910 and 2920. When the user selects the save feature, the program searches Table 3 to see if the saved entry is a new record or an existing record at step 2812. If this is a new record, the information is added to Table 3 at step 2814. If the saved record corresponds to an existing record, that record is changed to include the saved information at step 2816. Thus, Table 3 is updated with the changed information. The user can then enter more diagnoses through the diagnosis entry screen shown in FIG. 29, or the user can select the cancel feature. If the cancel feature is selected, the enter diagnosis screen of FIG. 29 is closed and the diagnosis list screen of FIG. 26 is displayed. If the user selects the more procedures feature at step 1816 in FIG. 18, the same type of process flow chart as that shown in FIG. 25 is utilized, except Table 2 in FIG. 24 is used instead of Table 3 in FIG. 27.

Figure 30:
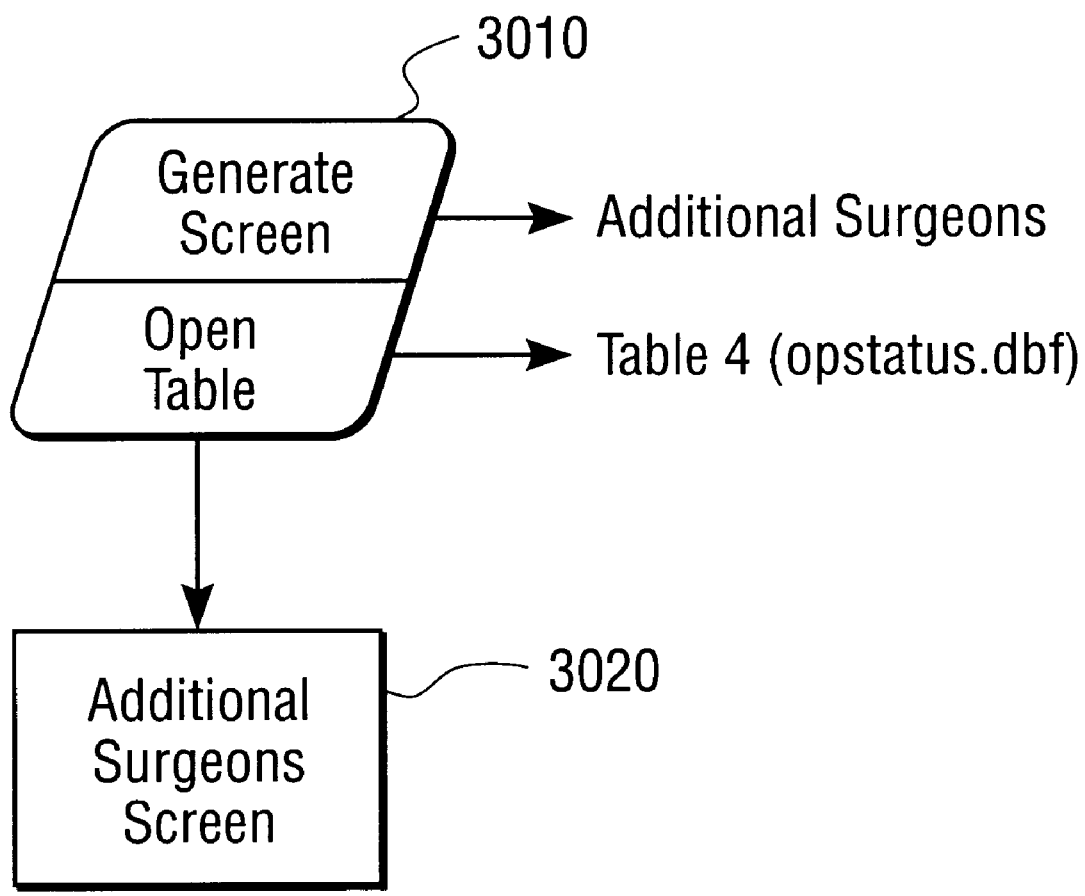
FIG. 30 is a process flow chart associated with the more surgeons feature.
Figures 32, 33:
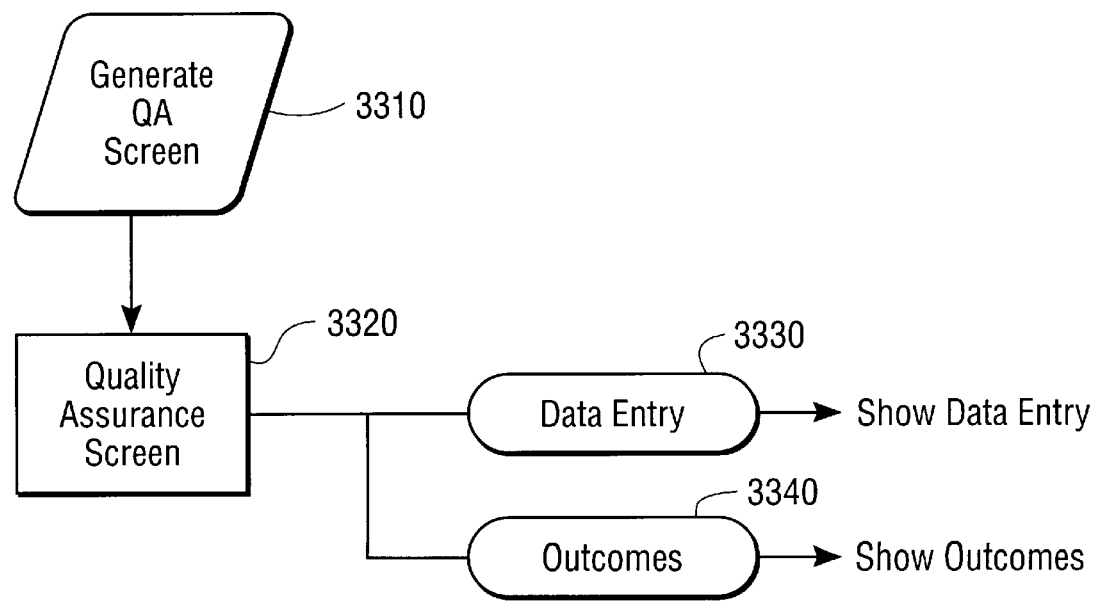
FIG. 32 is an example of Table 4 which includes information related to the fields listed in the Field Name column (e.g., OPSTATUSID, OPDATAID, SURGID, etc.)
FIG. 33 is a process flow chart associated with the QA feature.

FIG. 30 is a process flow chart associated with the more surgeons feature. At step 3010, the additional surgeons screen is generated and Table 4 is opened. FIG. 31 is an example of a screen display for entering additional surgeons. At step 3020, the additional surgeons screen shown in FIG. 31 is displayed. FIG. 32 is an example of Table 4 which includes information related to the fields listed in the Field Name column (e.g., OPSTATUSID, OPDATAID, SURGID, etc.). When the user inserts additional information into the additional surgeons screen shown in FIG. 31, Table 4 is utilized. The additional surgeons screen can, for example, include fields for the following: principle surgeon name, additional surgeon names, and procedures. New information is saved in Table 4 when the user selects the save feature in the additional surgeons screen. When the user selects the cancel feature in this screen, the program returns to the data entry screen shown at step 1812 in FIG. 18. If the user selects the main menu feature at step 1820 in FIG. 18, the data entry screen is closed and the program returns to the main menu screen at step 1612 in FIG. 16.

Figure 34:
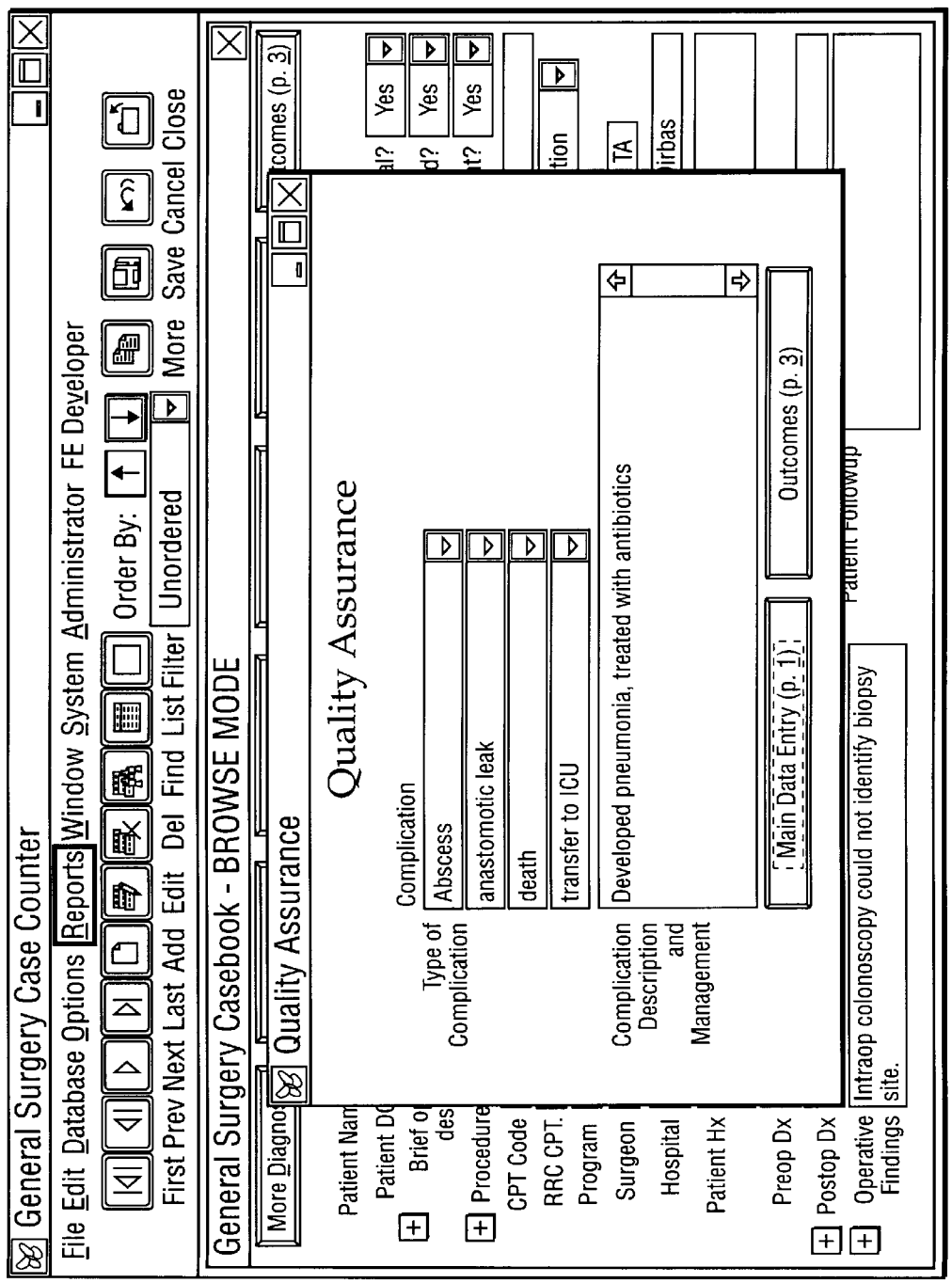
FIG. 34 is an example of a screen display for viewing quality assurance (QA) information.
Figure 35:
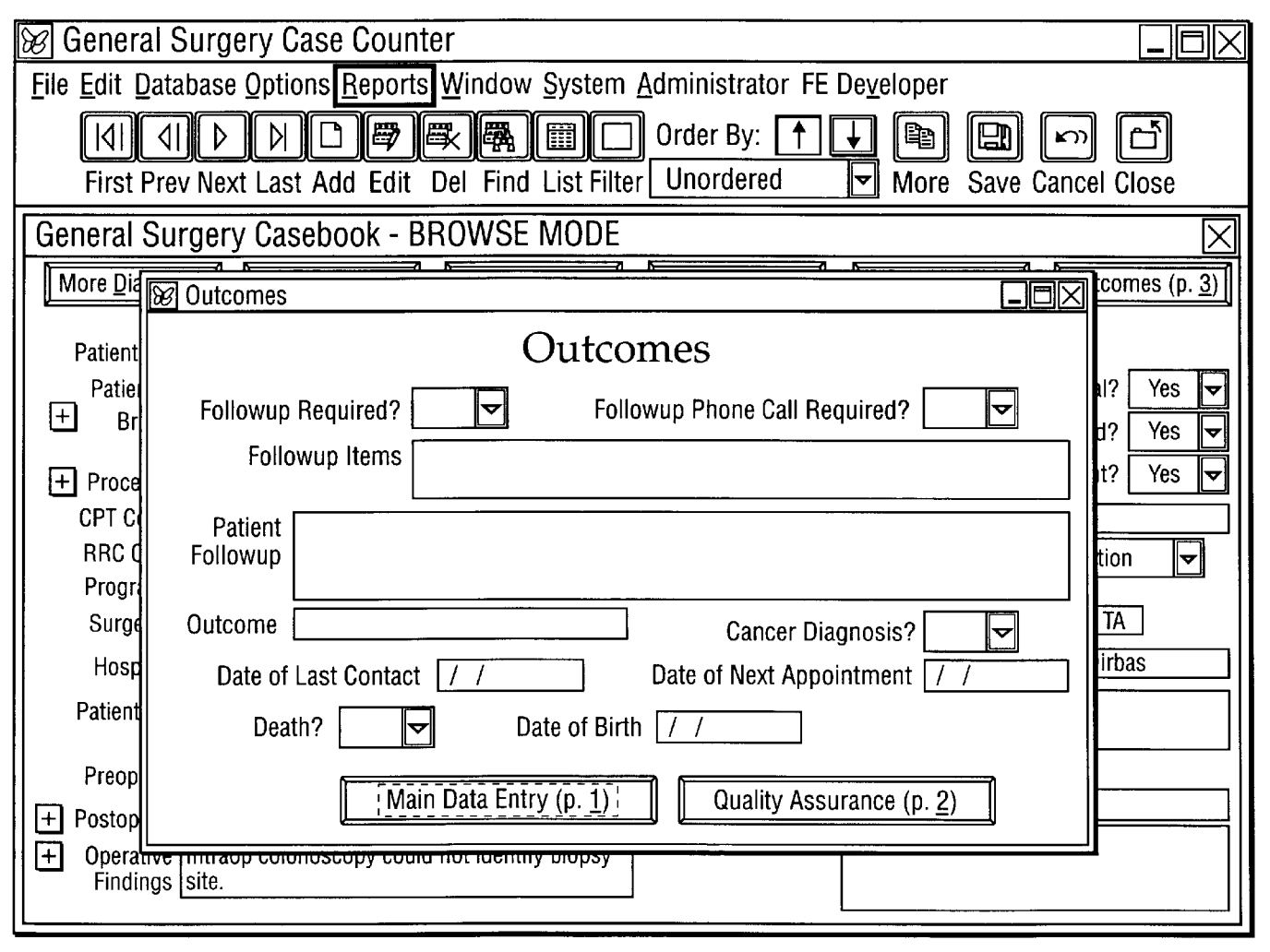

FIG. 33 is a process flow chart associated with the QA feature. At step 3310, the QA screen is generated. FIG. 34 is an example of a screen display for viewing quality assurance (QA) information. At step 3320, the quality assurance screen shown in FIG. 34 is displayed. The user can then scroll down through the quality assurance information which is available. For example, the user can view various types of complications, and complication description and management information. In the preferred embodiment, the QA screen is an overlay as shown in FIG. 34. When the user is done with the quality assurance information, the user can return to the data entry screen at step 3330, or the user can move on to the outcomes screen at step 3340. FIG. 35 is an example of a screen display for viewing outcomes information. The outcomes process flow chart is the same type of process flow chart as that for the QA feature shown in FIG. 33. In the preferred embodiment, the outcomes screen is an overlay as shown in FIG. 35. The data associated with the outcomes screen is set forth above and shown in FIG. 35.

Figure 36:
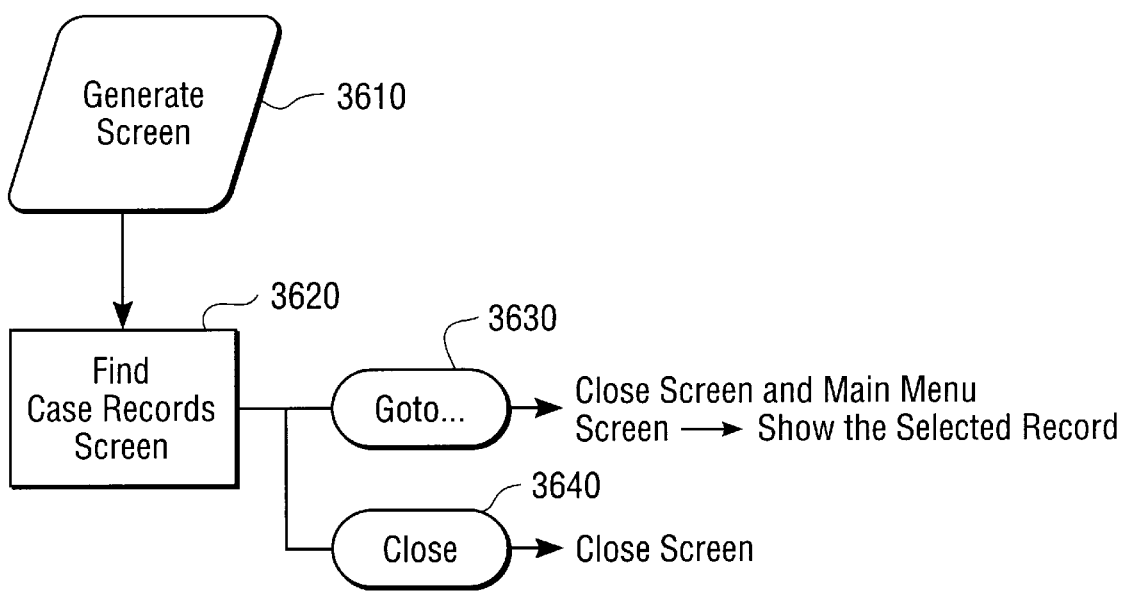
FIG. 36 is a process flow chart associated with the find feature.
Figure 37:
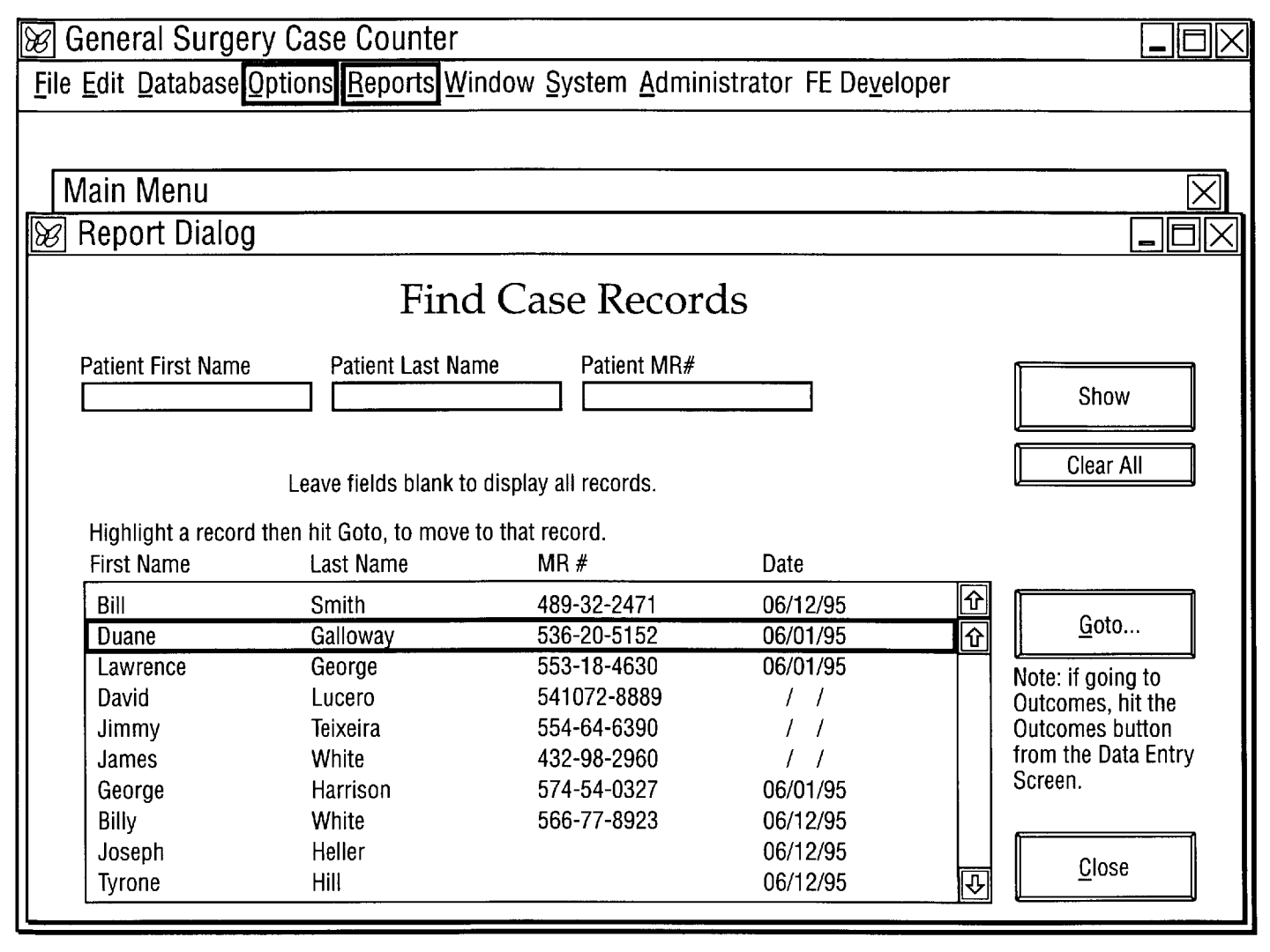

FIG. 36 is a process flow chart associated with the find feature. The find feature can be selected by the user at step 1616 in FIG. 16. At step 3610, the find case records screen is generated. FIG. 37 is an example of a screen display for the find case records feature. At step 3620, the find case records screen in FIG. 37 is displayed. The user can scroll through the information or search the information displayed in the find case records screen. Searches can be based on a patient's first name, a patients last name, or a patient's identification number (e.g., MR#). If the user selects the go to feature at step 3630, the find case records screen is closed and the main menu screen is displayed. If the user then selects the data entry feature at step 1614 in FIG. 16, the selected record (i.e., highlight record) from the find case records screen is automatically shown in the data entry screen. If the user selects the close feature at step 3640, the find case records screen is closed.

Figure 38:
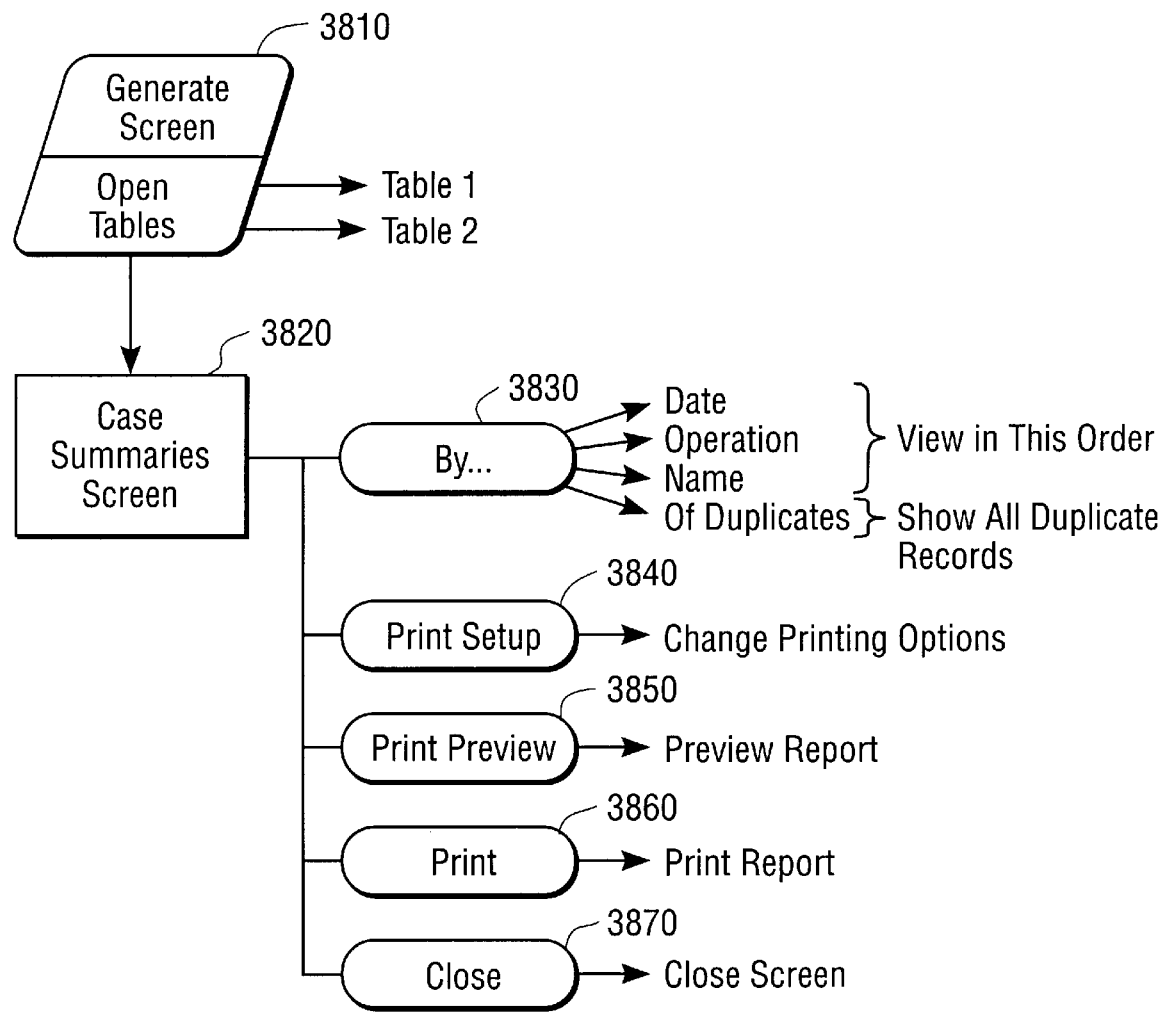
FIG. 38 is a process flow chart associate with the case review feature.

FIG. 38 is a process flow chart associate with the case review feature. At step 3810, the case summary screen is generated, and Tables 1 and 2 are opened. FIG. 39 is an example of a screen display for the case review feature which is entitled case summaries. Table 1 is the table in FIG. 23, and Table 2 is the table in FIG. 24. The case summary screen is displayed at step 3820. The entries in Table 1 of FIG. 23 are included in the case summary screen display. The order of the entries from Table 1 is determined by the user through the by . . . feature at step 3830. As the user scrolls through the by . . . feature, the user can determine the order in which the entries are displayed based on date, operation, name, or duplicates (i.e., show all duplicate entries first). At step 3840, the user can select the print setup feature to change the printing options. At step 3850, the user can select the print preview feature to preview a report. At step 3860, the user can select the print feature to print a report. At step 3870, the user can select the close feature to close the case summary screen and return to the main menu screen at step 1612 in FIG. 16. At step 1620, the user can select the import/export feature to allow for the import and/or the export of data files. At step 1622, the user can select the RRC reports feature.

Figure 40:
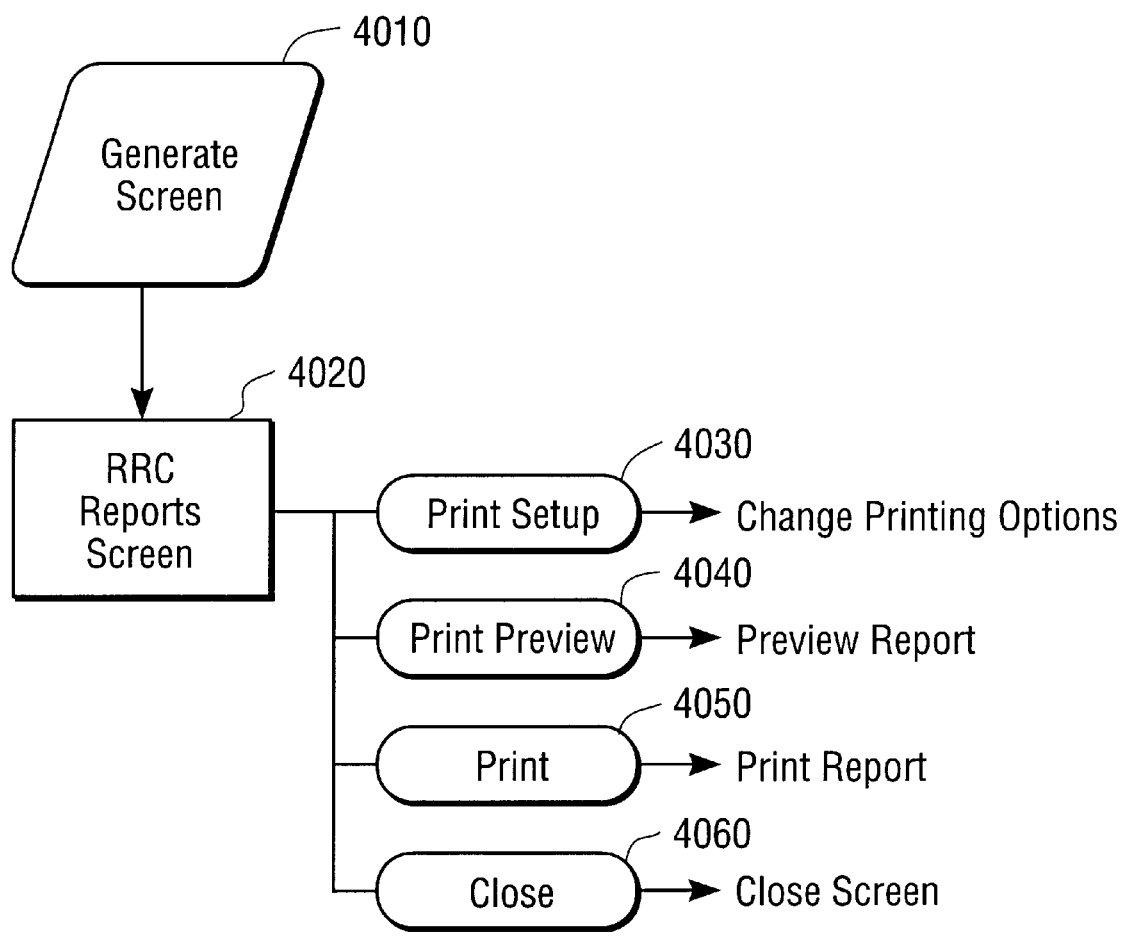
FIG. 40 is a process flow chart associated with the RRC reports feature.
Figure 41:
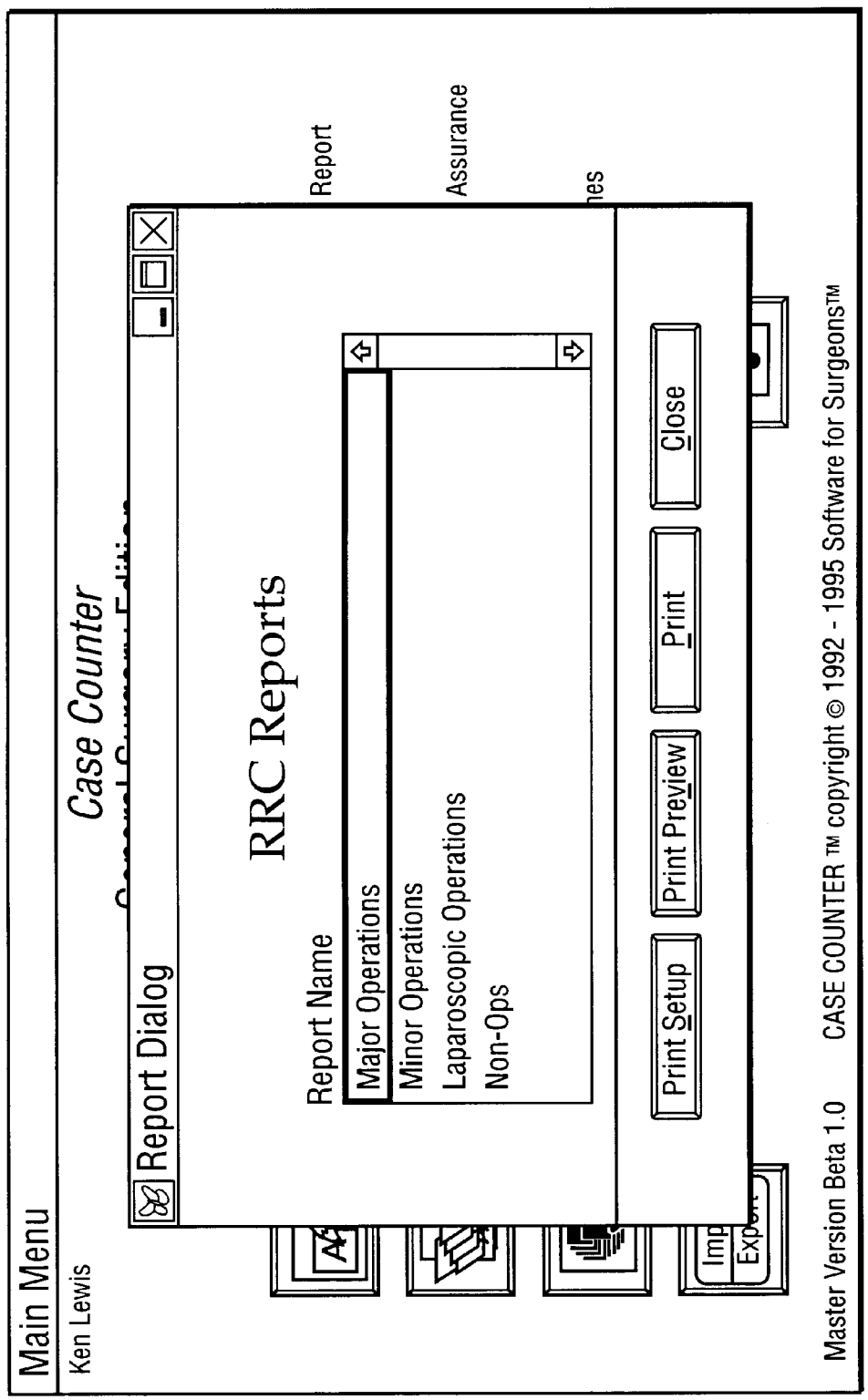
FIG. 41 is an example of a screen display for the RRC reports feature.

FIG. 40 is a process flow chart associated with the RRC reports feature. At step 4010, the RCC reports screen is generated. FIG. 41 is an example of a screen display for the RRC reports feature. The screen display in FIG. 41 is displayed at step 4020. At step 4030, the user can select the print setup feature to change the printing options. At step 4040, the user can select the print preview feature to preview a report corresponding to the highlighted entry in the RRC reports screen (e.g., see MAJOR OPERATIONS in FIG. 41). At step 4050, the user can select the print feature to print the report corresponding to the highlighted entry in the RRC report screen. At step 4060, the user can select the close feature to close the screen and return to the main menu screen at step 1612 in FIG. 16. At step 1624, the user can select the CPT reports feature. The CPT reports feature has the same type of process flow chart and screen display as that for the RRC reports feature set forth in FIGS. 40 and 41. At step 1626, the user can select the close case book feature to exit the application. At step 1628, the user can select the M and M report feature.

Figure 42:
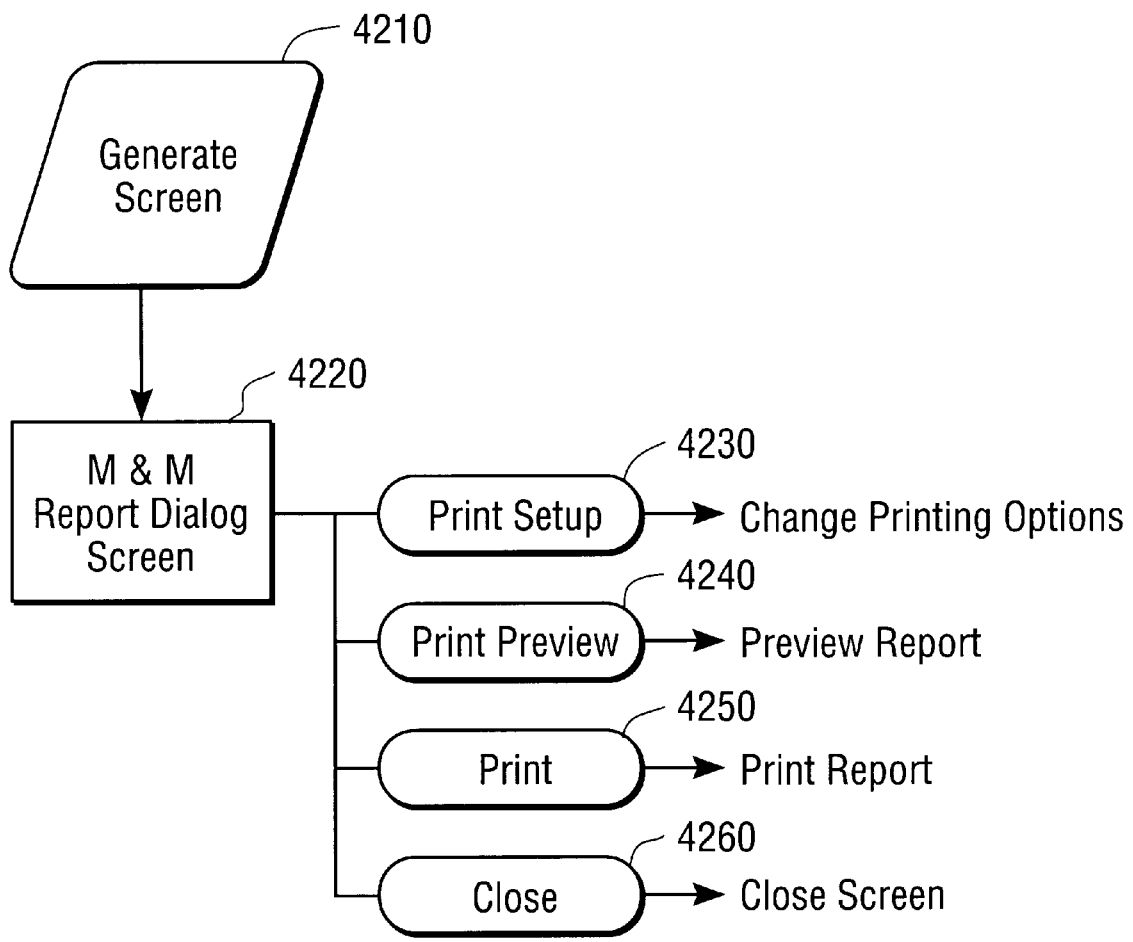
FIG. 42 is a process flow chart associated with the M and M report feature.
Figure 43:
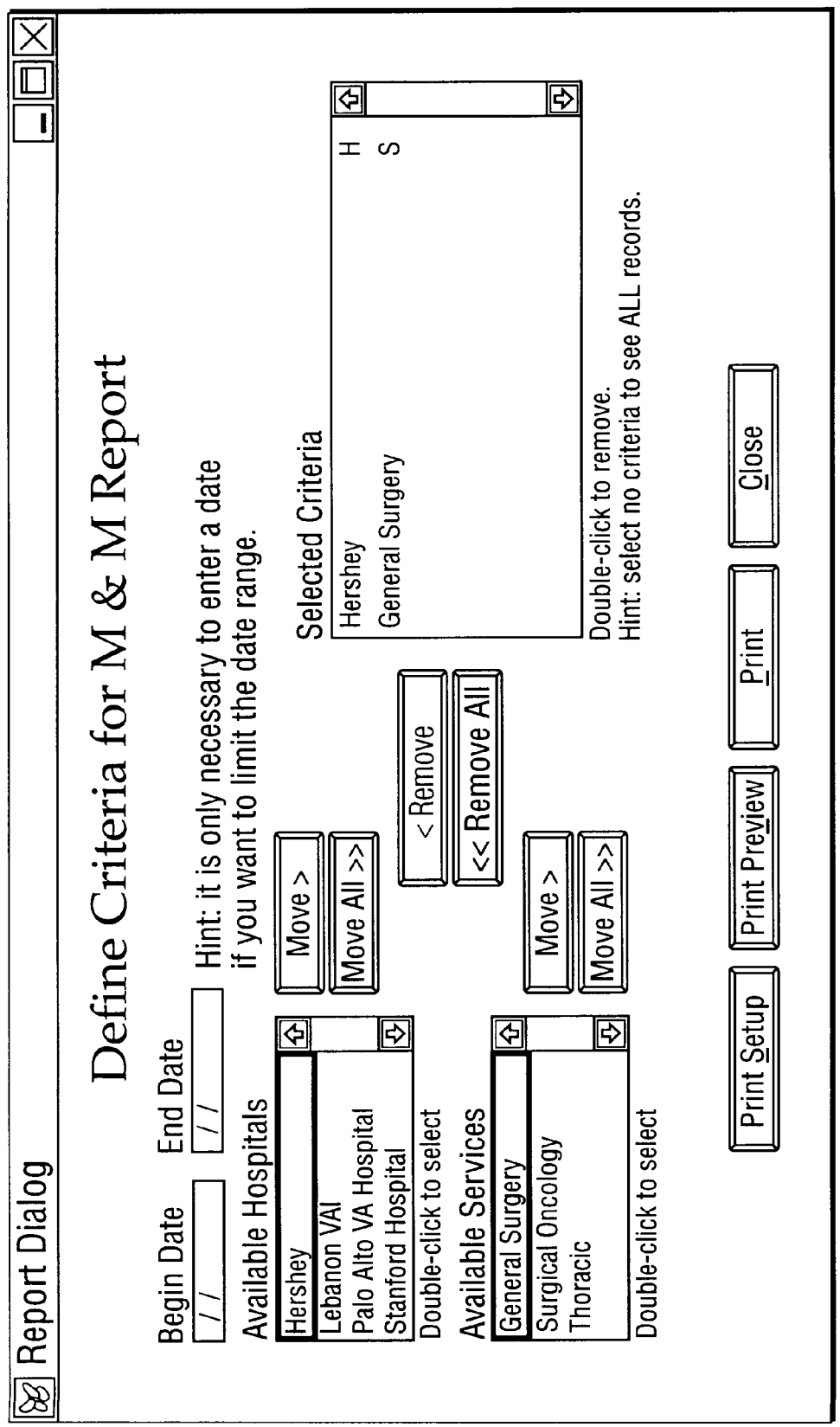
FIG. 43 is an example of a screen display for the M and M reports screen.

FIG. 42 is a process flow chart associated with the M and M report feature. M and M is used to indicate morbidity and mortality. At step 4210, the screen is generated. FIG. 43 is an example of a screen display for the M and M reports screen. At step 4220, the screen shown in FIG. 43 is displayed. This M and M report screen is used to define the criteria by which records will be filtered for the M and M report. These criteria can include, for example, an available hospital and/or an available service along with a specified time frame. At step 4230, the user can select the print setup feature to change the printing options for the M and M report. At step 4240, the user can select the print preview feature to preview the selected M and M report. At step 4250, the user can select the print feature to print the M and M report. At step 4260, the user can select the close feature to close the M and M reports screen shown in FIG. 43 and return to the main menu screen at step 1612 in FIG. 16. At step 1630, the user can select the quality assurance feature.

Figure 44:
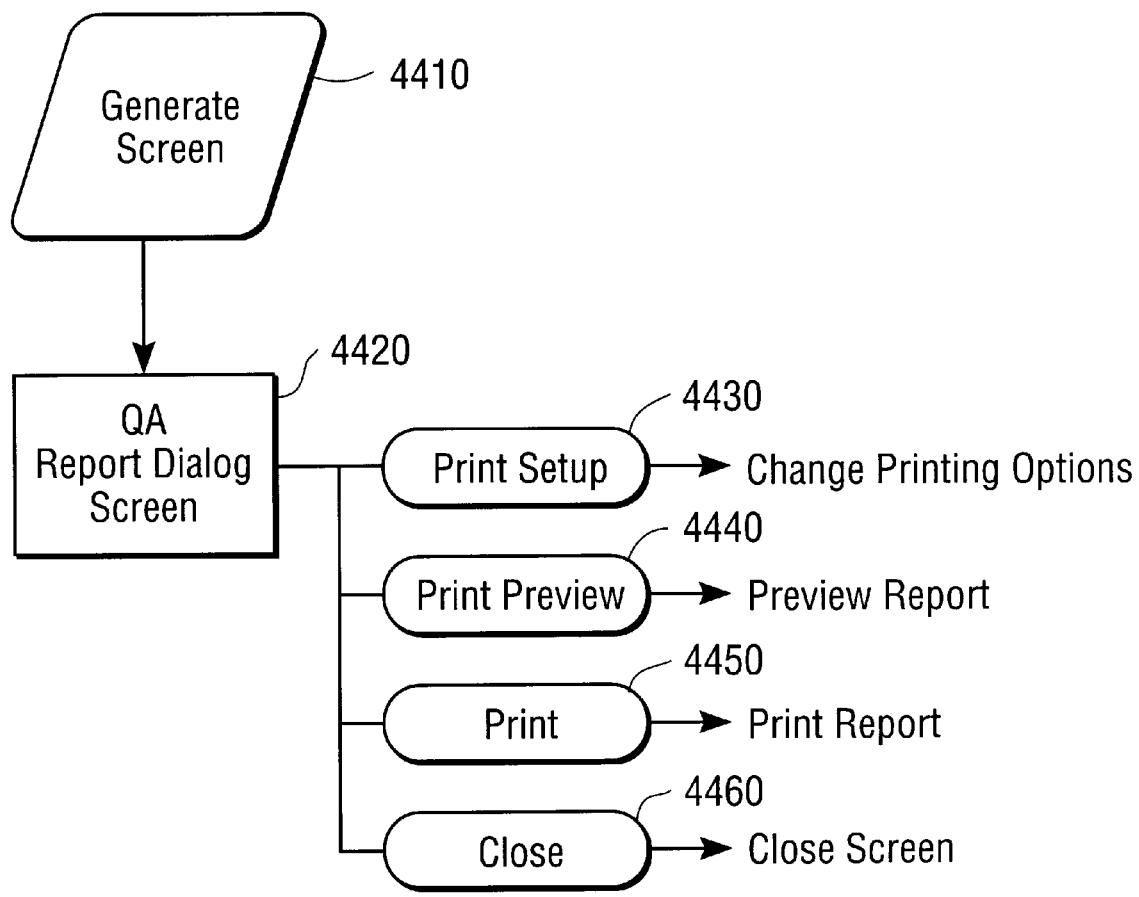
FIG. 44 is a process flow chart associated with the quality assurance feature.

FIG. 44 is a process flow chart associated with the quality assurance feature. At step 4410, the quality assurance (QA) document screen is generated. FIG. 45 is an example of a screen display for the QA document. At step 4420, the QA document screen shown in FIG. 45 is displayed. Again, the criteria for defining the QA document includes, for example, a patient's first name, a patient's last name, and a patient's identification number (e.g., MR#). At step 4430, the user can select the print setup feature to change the printing options for the QA document. At step 4440, the user can select the print preview feature to preview the record associated with the highlighted entry in the QA document screen. At step 4450, the user can select the print feature to print the record associated with the highlighted entry in the QA document screen. At step 4460, the user can select the close feature to close the QA document screen of FIG. 45 and return to the main menu screen at step 1612 in FIG. 16. The outcomes feature of step 1632 is described above. At step 1634, the user can select the help feature. The help feature retrieves the help file which includes searchable information about the software program. FIGS. 46A–D provide additional tables which can be used to assist in the generation of the above-described screens.

In yet another embodiment, the medical information log system of the present invention is used in conjunction with a Newton Message Pad or the like. The database within the message pad could be modified to track medical cases. In addition, the message pad could tie into the log system such that information could be entered and downloaded into the software database.

An example of pseudo-code for the present invention is included in the attached Appendix to further provide an example of how to implement the above described functionality in the preferred embodiment.

While a full and complete disclosure of the invention has been provided herein above, it will be obvious to those skilled in the art that various modifications and changes may be made.

What is claimed is:

1. In a computer system, a method of providing a medical information log system, comprising the steps of:

generating multiple screen displays;

inputting data for multiple medical log entries, said multiple screen displays assisting in said inputting of data, said medical log entries each being associated with information concerning a medical procedure, said information, including an identity of a doctor, a CPT code for billing, and being associated with a Resident Review Committee (RRC) code for tracking the medical procedure when performed by a resident;

storing said data in a memory within said computer system, said data being stored in an organized database;

retrieving desired data from said organized database, said multiple screen displays assisting a user in said retrieving of said desired data; and displaying said desired data within a portion of said multiple screen displays, wherein said data are related to multiple medical specialties.

2. The method of providing a medical information log system of claim 1, further comprising tracking said data for at least one of record keeping, outcome analysis, research, teaching, quality assurance, and billing.

3. The method of providing a medical information log system of claim 2, wherein said tracking is done in response to user inputs.

4. The method of providing a medical information log system of claim 1, wherein said multiple screen displays include at least one of a general surgery casebook screen, a diagnosis list screen, a RRC procedure list screen, an additional surgeons screen, a quality assurance screen, a M&M report screen, a RRC reports screen, a case summaries screen, an image data screen, an outcomes screen, an enter diagnosis screen, and a find case records screen.

5. The method of providing a medical information log system of claim 1, wherein said medical information log system is a surgical operative log system.

6. The method of providing a medical information log system of claim 1, wherein said medical procedure is related to a surgical operation.

7. The method of providing a medical information log system of claim 1, wherein said data includes RRC coding for each surgeon associated with said medical procedure.

8. The method of providing a medical information log system of claim 2, wherein said tracking is done with a controller.

9. The method of providing a medical information log system of claim 1, wherein said inputting is done with at least one of a mouse and a keyboard.

10. The computer system for providing said medical information log system of claim 1, made by the method of claim 1.

11. The method of providing a medical information log system of claim 1, wherein a computer program stored on a floppy disk assists with said generating, said inputting, said storing, said retrieving and said displaying.

12. The method of claim 1 wherein the RRC code is used for resident accreditation.

13. The method of claim 1 wherein the RRC code is established in part by the Accreditation Council for Graduate Medical Education (ACGME).

14. A computer system for providing a medical information log system, comprising:

an input device for inputting data for multiple log entries, said log entries each being associated with information concerning a medical procedure, said information, including an identity of a doctor, and being associated with a first set of consecutive alphanumeric characters, wherein said information corresponding to said medical procedure is augmented by associating a code with said medical procedure, said code including a second set of consecutive alphanumeric characters wherein said second set includes a subset of said first set and an additional alphanumeric character for generated an RRC code;

a memory for storing said data within said computer system, said data being stored in an organized database within said computer system;

a controller for tracking said data for at least two of record keeping, outcome analysis, research, teaching, quality assurance, and billing; and multiple screen displays for presenting said data when desired and for assisting in said inputting of said data;

wherein said data are related to multiple medical specialties and said medical information log system is configured to support review of said data by at least one of said information identifying at least one doctor, and said code.

15. The computer system for providing a medial information log system of claim 14, wherein said input device is done with at least one of a mouse and a keyboard.

16. In a computer system, a method of providing a medical information log system, comprising the steps of:

generating prompts on a screen in said computer system, said prompts being displayed to a user;

inputting data for multiple log entries, said prompts assisting in said inputting of data, said log entries each being associated with information concerning a medical procedure, said information, including an identity of a doctor, and being associated with a first set of consecutive alphanumeric characters, wherein said information corresponding to said medical procedure is augmented by associating a code with said medical procedure, said code including a second set of consecutive alphanumeric characters wherein said second set includes a subset of said first set and an additional alphanumeric character for generating an RRC code;

storing said data in a memory within said computer system, said data being stored in an organized database within said computer system;

tracking said data for at least one of record keeping, outcome analysis, research, teaching, quality assurance, and billing, said tracking being done in response to user inputs;

retrieving desired data from said organized database, said prompts assisting the user in said retrieving of said desired data; and displaying said data on said screen when desired;

wherein said data are related to multiple medical specialties, and wherein a computer program stored on a floppy disk assists with said generating, said inputting, said storing, said tracking, said retrieving and said displaying, and wherein said medical information log system is configured to support review of said data by at least one of said information identifying at least one doctor, and said code.

17. The computer system for providing said medical information log system of claim 16, made by the method of claim 16.

* * * * *